United States Patent
Godfrey, Jr. et al.

(10) Patent No.: US 6,867,300 B2
(45) Date of Patent: Mar. 15, 2005

(54) METHODS FOR THE PREPARATION OF PYRROLOTRIAZINE COMPOUNDS USEFUL AS KINASE INHIBITORS

(75) Inventors: Jollie Duaine Godfrey, Jr., Ewing, NJ (US); John Hynes, Jr., Washington Crossing, PA (US); Alaric J. Dyckman, Lawrenceville, NJ (US); Katerina Leftheris, Skillman, NJ (US); Zhongping Shi, West Windsor, NJ (US); Stephen T. Wrobleski, Whitehouse Station, NJ (US); Wendel William Doubleday, Doylestown, PA (US); John A. Grosso, Princeton Junction, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 60 days.

(21) Appl. No.: 10/289,010

(22) Filed: Nov. 6, 2002

(65) Prior Publication Data

US 2003/0186982 A1 Oct. 2, 2003

Related U.S. Application Data

(63) Continuation-in-part of application No. 10/036,293, filed on Nov. 7, 2001, now Pat. No. 6,670,357.
(60) Provisional application No. 60/249,877, filed on Nov. 17, 2000, and provisional application No. 60/310,561, filed on Aug. 7, 2001.

(51) Int. Cl.$^7$ .................. C07D 487/04; A61K 31/53; A61P 19/02; A61P 11/06; A61P 19/10
(52) U.S. Cl. .................................................. 544/183
(58) Field of Search ........................................ 544/183

(56) References Cited

U.S. PATENT DOCUMENTS

| | | | |
|---|---|---|---|
| 5,658,903 A | 8/1997 | Adams et al. | 514/235.8 |
| 5,932,576 A | 8/1999 | Anantanarayan et al. | 514/235.5 |
| 5,945,418 A | 8/1999 | Bemis et al. | 514/258 |
| 5,977,103 A | 11/1999 | Adams et al. | 514/235.2 |
| 6,087,496 A | 7/2000 | Anantanarayan et al. | 514/124 |
| 6,130,235 A | 10/2000 | Mavunkel et al. | 514/322 |
| 6,147,080 A | 11/2000 | Bemis et al. | 514/248 |
| 6,251,914 B1 | 6/2001 | Adams et al. | 514/274 |
| 6,277,989 B1 | 8/2001 | Chakravarty et al. | 544/393 |

FOREIGN PATENT DOCUMENTS

| | | |
|---|---|---|
| EP | 0713876 | 5/1996 |
| EP | 0778277 A1 | 11/1997 |
| WO | WO9924033 | 5/1999 |
| WO | WO 00/12074 | 3/2000 |
| WO | WO 00/12497 | 3/2000 |
| WO | WO 00/56738 | 9/2000 |
| WO | WO 00/71129 A1 | 11/2000 |
| WO | WO 01/14378 A1 | 3/2001 |
| WO | WO 01/27089 A1 | 4/2001 |
| WO | WO 01/34605 A1 | 5/2001 |
| WO | WO01/47897 | 7/2001 |

OTHER PUBLICATIONS

Patil, S. A., et al., "Synthesis of Pyrrolo[2,1-f][1,2,4]triazine Congeners of Nucleic Acid Purines via the N–Amination of 2–Substituted Pyrroles [1]", Journal of Heterocyclic Chemistry, 1994, vol. 31, pp. 781–786.

Shen, Y. et al., "Comparison of Electrophilic Amination Reagents for N–Amination of 2–Oxazolidinones and Application to Synthesis of Chiral Hydrazones", J. Org. Chem., 2002, vol. 67, pp. 6236–6239.

Moreland et al.; American College of Physicians—Am. Soc. of Internal Medicine; vol. 130; pp. 478–486 (1999).

Henry et al.; Drugs of the Future 24(12) pp. 1345–1354 (1999).

Rankin et al.; British Journal of Rhematology, 34, pp. 334–342 (1995).

Salituro et al., Current Medicinal Chemistry; 6 pp. 807–823 (1999).

*Primary Examiner*—Mukund J. Shah
*Assistant Examiner*—Kahsay Habte
(74) *Attorney, Agent, or Firm*—Henry H. Gu

(57) ABSTRACT

Methods of preparing kinase inhibiting pharmaceutical compounds having the formula (I):

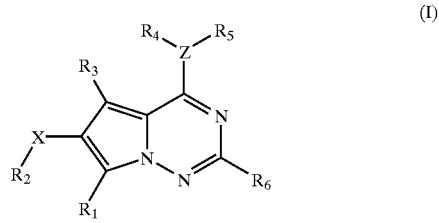

or a pharmaceutically acceptable salt or solvate thereof, wherein $R_1$ through $R_6$ and Z are as described in the specification. The methods according to the invention utilize an amination process, in which a pyrrole is reacted with a haloamine, preferably chloramine. This step is followed by cyclization to form the pyrrolotriazine core.

9 Claims, No Drawings

METHODS FOR THE PREPARATION OF PYRROLOTRIAZINE COMPOUNDS USEFUL AS KINASE INHIBITORS

BASIS FOR PRIORITY CLAIM

This application is a continuation-in-part of U.S. application Ser. No. 10/036,293, filed Nov. 7, 2001, now U.S. Pat. No. 6,670,357, which claims priority of U.S. Provisional Application Ser. No. 60/249,877, filed Nov. 17, 2000, and U.S. Provisional Ser. No. 60/310,561, filed Aug. 7, 2001. The entire disclosure of each of the foregoing applications is herein incorporated by reference in its entirety.

FIELD OF THE INVENTION

The invention relates to methods for preparing pyrrolotriazine pharmaceutical compounds having activity as kinase inhibitors and, in particular, to methods for making pyrrolotriazine-containing compounds useful for treating kinase-associated conditions. The invention also includes an efficient method of aminating pyrrole compounds useful in the synthesis of pyrrolotriazines and other N-aminated heterocyclic compounds.

BACKGROUND OF THE INVENTION

The invention generally relates to methods for preparing compounds useful as kinase inhibitors or alternatively, as components or precursors in the synthesis of kinase inhibitors.

Pyrrolotriazine compounds useful as kinase inhibitors are disclosed in U.S. patent application Ser. No. 09/573,829 filed May 18, 2000, which is commonly assigned with this application. Pyrrolotriazine compounds substituted with an acidic group reportedly having sPLA$_2$-inhibitory activity are disclosed in WO 01/14378 A1 to Shionogi & Co., Ltd, published Mar. 1, 2001 in Japanese. The entire disclosure of each of the patent applications, patents, and publications referred to herein is incorporated herein by reference.

Compounds suitable as kinase inhibitors are described in co-pending and commonly assigned U.S. application Ser. No. 10/036,293, the entire disclosure of which is herein incorporated by reference. There are no previously known methods for manufacturing pyrrolotriazines, which form the core structure of such kinase inhibitors. Desirably, useful processes for producing such compounds would utilize commercially available starting materials to minimize costs, and would also reduce the reliance on more toxic reactants, while maintaining acceptable product yields. Such processes are described and claimed herein.

SUMMARY OF THE INVENTION

The presently claimed invention is directed, in one aspect, to a method of forming a heterocyclic pyrrole-containing reaction product by first aminating a pyrrole using a haloamine, preferably chloramine, as the aminating agent. The aminated pyrrole-containing compound may then be cyclized to form a pyrrolotriazine. In one aspect therefore, the invention comprises reacting a pyrrole-containing compound of Formula IV:

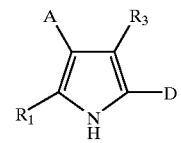

IV wherein $R_1$ is selected from H, alkyl, aralkyl, $OR_1'$, $OC(O)R_1'$, $OC(O)OR_1'$, $OC(O)NR_1'R_1''$, $OS(O)_2R'''$, and $OS(O)_2NR_1'R_1'''$, wherein the groups $R_1'$ and $R_1''$ may each independently be H, alkyl, aryl, aralkyl, heterocyclo, or cycloalkyl groups, or may be taken together to form a cycloalkyl, aryl, or heterocyclic group, any of which may be optionally substituted, and the group $R_1'''$ is defined as an alkyl, aryl, aralkyl, heterocyclo, or cycloalkyl; —$SCH_3$, —$OC(=O)R_{21}$, —$S(=O)R_{22}$, —$SO_2R_{22}$, —$SO_2NR_{24}R_{25}$, —$CO_2R_{21}$, —$C(=O)NR_{24}R_{25}$, —$NH_2$, —$NR_{24}R_{25}$, —$NR_{21}SO_2NR_{24}R_{25}$, —$NR_{21}SO_2R_{22}$, —$NR_{24}C(=O)R_{25}$, —$NR_{24}CO_2R_{25}$, —$NR_{21}C(=O)NR_{24}R_{25}$, halogen, nitro, or cyano;

A is selected from $R_2X$ or E, where X is selected from the group consisting of —O—, —OC(=O)—, —S—, —S(=O)—, —$SO_2$—, —C(=O)—, —$CO_2$—, —$NR_{10}$—, —$NR_{10}C(=O)$—, —$NR_{10}C(=O)NR_{11}$—, —$NR_{10}CO_2$—, —$NR_{10}SO_2$—, —$NR_{10}SO_2NR_{11}$—, —$SO_2NR_{10}$—, —$C(=O)NR_{10}$—, halogen, nitro, and cyano, or X is absent; and E is an electron withdrawing group; or $R_1$, taken together with A, can form an optionally substituted saturated or unsaturated aromatic or heterocyclic ring;

$R_2$ is selected from:
  (i) hydrogen, provided that $R_2$ is not hydrogen if X is —S(=O)—, —$SO_2$—, —$NR_{10}CO_2$—, or —$NR_{10}SO_2$—;
  (ii) alkyl, alkenyl, and alkynyl optionally substituted with up to four $R_{26}$;
  (iii) aryl and heteroaryl optionally substituted with up to three $R_{27}$;
  (iv) heterocyclo and cycloalkyl optionally substituted with keto (=O), up to three $R_{27}$, and/or having a carbon-carbon bridge of 3 to 4 carbon atoms; or
  (v) —$C(O)R^b$ where $R^b$ is H, OH, alkyl, aralkyl, halo, $OR^{b'}$, $OC(O)R^{b'}$, $OC(O)OR^{b'}$, $OC(O)NR^bR^{b'}$, $OS(O)R^{b'}$, $OS(O)NR^bR^{b'}$, and $R^b$ and $R^{b'}$ are each independently selected from H, alkyl, aralkyl, heterocyclo or cycloalkyl, or $R^b$ and $R^{b'}$ together form a cycloalkyl, aryl or heterocyclo group; however $R_2$ is absent if X is halogen, nitro or cyano;

$R_3$ is selected from H, OH, $C_1$-$C_6$ alkoxy, alkyl, $C_1$-$C_6$ perfluoroalkyl, —O—($C_1$-$C_6$) perfluoroalkyl, cycloalkyl, heterocyclo, aryl, aralkyl, acyl, carbalkoxy, carboxamido, cyano, halogen, amine, substituted amine, $NO_2$, $OR_3'$, $CH_2OR_3'$, $CH_2NR_3'R_3''$, $CH_2SR_3'$, $OC(O)R_3'$, $OC(O)OR_3'$, $OC(O)NR_3'R_3''$, $OS(O)_2R_3'$, and $OS(O)_2NR_3'R_3''$; the $R_3'$ and $R_3''$ groups are each independently H, alkyl, aralkyl, heterocyclo, cycloalkyl, or aryl. $R_3'$ and $R_3''$ when taken together may form a cycloalkyl, aryl, or heterocyclic group, any of which may be optionally substituted;

$R_7$, $R_8$, $R_{21}$, $R_{24}$, and $R_{25}$ are independently selected from hydrogen, alkyl, substituted alkyl, aryl, substituted aryl, heterocyclo, and substituted heterocyclo;

$R_{10}$ and $R_{11}$ are independently selected from hydrogen, alkyl, substituted alkyl, aryl, substituted aryl, cycloalkyl, substituted cycloalkyl, heterocyclo, and substituted heterocyclo;

$R_{22}$ is selected from alkyl, substituted alkyl, aryl, substituted aryl, heterocyclo, or substituted heterocyclo;

$R_{26}$ is selected from halogen, trifluoromethyl, haloalkoxy, keto (=O), nitro, cyano, —$SR_{28}$, —$OR_{28}$, —$NR_{28}R_{29}$, —$NR_{28}SO_2$, —$NR_{28}SO_2R_{29}$, —$SO_2R_{28}$, —$SO_2NR_{28}R_{29}$, —$CO_2R_{28}$, —$C(=O)R_{28}$, —$C(=O)NR_{28}R_{29}$, —$OC(=O)R_{28}$, —$OC(=O)NR_{28}R_{29}$, —$NR_{28}C(=O)R_{29}$, —$NR_{28}CO_2R_{29}$, =N—OH, =N—O-alkyl; aryl optionally substituted with one to three $R_{27}$; cycloalkyl optionally substituted with keto (=O), one to three $R_{27}$, or having a carbon-carbon bridge of 3 to 4 carbon atoms; and heterocyclo optionally substituted with keto (=O), one to three $R_{27}$, or having a carbon-carbon bridge of 3 to 4 carbon atoms; wherein $R_{28}$ and $R_{29}$ are each independently selected from hydrogen, alkyl, alkenyl, aryl, aralkyl, $C_{3-7}$cycloalkyl, and $C_{3-7}$heterocycle, or may be taken together to form a $C_{3-7}$heterocycle; and wherein each $R_{28}$ and $R_{29}$ in turn is optionally substituted with up to two of alkyl, alkenyl, halogen, haloalkyl, haloalkoxy, cyano, nitro, amino, hydroxy, alkoxy, alkylthio, phenyl, benzyl, phenyloxy, and benzyloxy;

$R_{27}$ is selected from alkyl, $R_{32}$, and $C_{1-4}$alkyl substituted with one to three $R_{32}$, wherein each $R_{32}$ group is independently selected from halogen, haloalkyl, haloalkoxy, nitro, cyano, —$SR_{30}$, —$OR_{30}$, —$NR_{30}R_{31}$, —$NR_{30}SO_2$, —$NR_{30}SO_2R_{31}$, —$SO_2R_{30}$, —$SO_2NR_{30}R_{31}$, —$CO_2R_{30}$, —$C(=O)R_{30}$, —$C(=O)NR_{30}R_{31}$, —$OC(=O)R_{30}$, —$OC(=O)NR_{30}R_{31}$, —$NR_{30}C(=O)R_{31}$, —$NR_{30}CO_2R_{31}$, and a 3 to 7 membered carbocyclic or heterocyclic ring optionally substituted with alkyl, halogen, hydroxy, alkoxy, haloalkyl, haloalkoxy, nitro, amino, or cyano, wherein $R_{30}$ and $R_{31}$ are independently selected from hydrogen, alkyl, alkenyl, aryl, aralkyl, $C_{3-7}$cycloalkyl, and heterocycle, or may be taken together to form a $C_{3-7}$ heterocycle; and D is selected from the group consisting of —CHO, CN, —$COR_p$, —$C(=O)OR_p$, or $R_qC(O)NH—$, where $R_p$ and $R_q$ are each independently selected from H or substituted or unsubstituted $C_1$–$C_6$ alkyl, aryl or halogenated alkyl;

with chloramine, in the presence of a suitable base, to form a compound of Formula V:

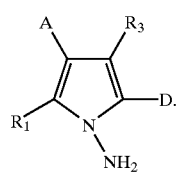

V

In another aspect, the invention comprises a process of making one or more pharmaceutically active compounds effective at inhibiting kinase activity having the formula I:

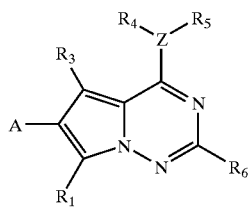

(I)

and pharmaceutically acceptable salts or solvates thereof; wherein $R_1$ is selected from H, alkyl, aralkyl, $OR_1'$, $OC(O)R_1'$, $OC(O)OR_1'$, $OC(O)NR_1'R_1''$, $OS(O)_2R_1'''$, and $OS(O)_2NR_1'R_1''$, wherein the groups $R_1'$ and $R_1''$ may each independently be H, alkyl, aryl, aralkyl, heterocyclo, or cycloalkyl groups, or may be taken together to form a cycloalkyl, aryl, or heterocyclic group, any of which may be optionally substituted, and the group $R_1'''$ is defined as an alkyl, aryl, aralkyl, heterocyclo, or cycloalkyl; —$SCH_3$, —$OC(=O)R_{21}$, —$S(=O)R_{22}$, —$SO_2R_{22}$, —$SO_2NR_{24}R_{25}$, —$CO_2R_{21}$, —$C(=O)NR_{24}R_{25}$, —$NH_2$, —$NR_{24}R_{25}$, —$NR_{21}SO_2NR_{24}R_{25}$, —$NR_{21}SO_2R_{22}$, —$NR_{24}C(=O)R_{25}$, —$NR_{24}CO_2R_{25}$, —$NR_{21}C(=O)NR_{24}R_{25}$, halogen, nitro, or cyano;

A is selected from $R_2X$ or E, where X is selected from the group consisting of —O—, —OC(=O)—, —S—, —S(=O)—, —$SO_2$—, —C(=O)—, —$CO_2$—, —$NR_{10}$—, —$NR_{10}C(=O)$—, —$NR_{10}C(=O)NR_{11}$—, —$NR_{10}CO_2$—, —$NR_{10}SO_2$—, —$NR_{10}SO_2NR_{11}$—, —$SO_2NR_{10}$—, —$C(=O)NR_{10}$—, halogen, nitro, and cyano, or X is absent; and E is an electron withdrawing group; or $R_1$, taken together with A, can form an optionally substituted saturated or unsaturated aromatic or heterocyclic ring;

$R_2$ is selected from:
(i) hydrogen, provided that $R_2$ is not hydrogen if X is —S(=O)—, —$SO_2$—, —$NR_{10}CO_2$—, or —$NR_{10}SO_2$—;
(ii) alkyl, alkenyl, and alkynyl optionally substituted with up to four $R_{26}$;
(iii) aryl and heteroaryl optionally substituted with up to three $R_{27}$;
(iv) heterocyclo and cycloalkyl optionally substituted with keto (=O), up to three $R_{27}$, and/or having a carbon-carbon bridge of 3 to 4 carbon atoms; or
(v) —$C(O)R^b$ where $R^b$ is H, OH, alkyl, aralkyl, halo, $OR^{b'}$, $OC(O)R^{b'}$, $OC(O)OR^{b'}$, $OC(O)NR^bR^{b'}$, $OS(O)R^{b'}$, $OS(O)NR^bR^{b'}$, and $R^b$ and $R^{b'}$ are each independently selected from H, alkyl, aralkyl, heterocyclo or cycloalkyl, or or $R^b$ and $R^{b'}$ together form a cycloalkyl, aryl or heterocyclo group; however $R_2$ is absent if X is halogen, nitro or cyano;

$R_3$ is selected from H, OH, $C_1$–$C_6$ alkoxy, alkyl, $C_1$–$C_6$ perfluoroalkyl, —O—$C_1$–$C_6$ perfluoroalkyl, cycloalkyl, heterocyclo, aryl, aralkyl, acyl, carbalkoxy, carboxamido, cyano, halogen, amine, substituted amine, $NO_2$, $OR_3'$, $CH_2OR_3'$, $CH_2NR_3'R_3''$, $CH_2SR_3'$, $OC(O)R_3'$, $OC(O)OR_3''$, $OC(O)NR_3'R_3''$, $OS(O)_2R_3'$, and $OS(O)_2NR_3'R_3''$; the $R_3'$ and $R_3''$ groups are each independently H, alkyl, aralkyl, heterocycle, cycloalkyl, or aryl. $R_3'$ and $R_3''$ when taken together may form a cycloalkyl, aryl, or heterocyclic group, any of which may be optionally substituted;

Z is selected from O, S or N;

$R^4$ is selected from substituted aryl, aryl substituted with NHSO$_2$alkyl, substituted heteroaryl, or an optionally-substituted bicyclic 7–11 membered saturated or unsaturated carbocyclic or heterocyclic ring, and $R_5$ is hydrogen, alkyl, or substituted alkyl; provided that when Z is O or S, one of $R_4$ or $R_5$ is absent; or alternatively, $R_4$ and $R_5$ taken together with Z form an optionally substituted aryl, or an optionally-substituted bicyclic 7–11 membered aryl or heteroaryl; wherein in either case the substitution of the aryl or the bicyclic aryl or heteroaryl may be by a substituted or unsubstituted alkyl, cycloalkyl, aryl or heteroaryl substituent;

$R_6$ is selected from hydrogen, alkyl, substituted alkyl, cycloalkyl, aryl, substituted aryl, aralkyl, heterocyclo, substituted heterocyclo, —NR$_7$R$_8$, —OR$_7$, acyl, carbalkoxy, carboxamido or halogen; wherein the carbalkoxy, acyl, and carboxamido groups are optionally substituted with one or two substituent groups, each of which is independently H, alkyl, aralkyl, or heterocyclo;

$R_{10}$ and $R_{11}$ are independently selected from hydrogen, alkyl, substituted alkyl, aryl, substituted aryl, cycloalkyl, substituted cycloalkyl, heterocyclo, and substituted heterocyclo;

$R_7$, $R_8$, $R_{21}$, $R_{24}$, and $R_{25}$ are independently selected from hydrogen, alkyl, substituted alkyl, aryl, substituted aryl, heterocyclo, and substituted heterocyclo;

$R_{22}$ is selected from alkyl, substituted alkyl, aryl, substituted aryl, heterocyclo, or substituted heterocyclo;

$R_{26}$ is selected from halogen, trifluoromethyl, haloalkoxy, keto (=O), nitro, cyano, —SR$_{28}$, —OR$_{28}$, —NR$_{28}$R$_{29}$, —NR$_{28}$SO$_2$, —NR$_{28}$SO$_2$R$_{29}$, —SO$_2$R$_{28}$, —SO$_2$NR$_{28}$R$_{29}$, —CO$_2$R$_{28}$, —C(=O)R$_{28}$, —C(=O)NR$_{28}$R$_{29}$, —OC(=O)R$_{28}$, —OC(=O)NR$_{28}$R$_{29}$, —NR$_{28}$C(=O)R$_{29}$, —NR$_{28}$CO$_2$R$_{29}$, =N—OH, =N—O-alkyl; aryl optionally substituted with one to three R$_{27}$; cycloalkyl optionally substituted with keto (=O), one to three R$_{27}$, or having a carbon-carbon bridge of 3 to 4 carbon atoms; and heterocyclo optionally substituted with keto (=O), one to three R$_{27}$, or having a carbon-carbon bridge of 3 to 4 carbon atoms; wherein R$_{28}$ and R$_{29}$ are each independently selected from hydrogen, alkyl, alkenyl, aryl, aralkyl, C$_{3-7}$cycloalkyl, and C$_{3-7}$heterocycle, or may be taken together to form a C$_{3-7}$ heterocycle; and wherein each R$_{28}$ and R$_{29}$ in turn is optionally substituted with up to two of alkyl, alkenyl, halogen, haloalkyl, haloalkoxy, cyano, nitro, amino, hydroxy, alkoxy, alkylthio, phenyl, benzyl, phenyloxy, and benzyloxy; and $R_{27}$ is selected from alkyl, R$_{32}$, and C$_{1-4}$alkyl substituted with one to three R$_{32}$, wherein each R$_{32}$ group is independently selected from halogen, haloalkyl, haloalkoxy, nitro, cyano, —SR$_{30}$, —OR$_{30}$, —NR$_{30}$R$_{31}$, —NR$_{30}$SO$_2$, —NR$_{30}$SO$_2$R$_{31}$, —SO$_2$R$_{30}$, —SO$_2$NR$_{30}$R$_{31}$, —CO$_2$R$_{30}$, —C(=O)R$_{30}$, —C(=O)NR$_{30}$R$_{31}$, —OC(=O)R$_{30}$, —OC(=O)NR$_{30}$R$_{31}$, —NR$_{30}$C(=O)R$_{31}$, —NR$_{30}$CO$_2$R$_{31}$, and a 3 to 7 membered carbocyclic or heterocyclic ring optionally substituted with alkyl, halogen, hydroxy, alkoxy, haloalkyl, haloalkoxy, nitro, amino, or cyano, wherein R$_{30}$ and R$_{31}$ are each independently selected from hydrogen, alkyl, alkenyl, aryl, aralkyl, C$_{3-7}$cycloalkyl, and heterocycle, or may be taken together to form a C$_{3-7}$ heterocycle;

the method comprising:

a) reacting a pyrrole compound of Formula IV:

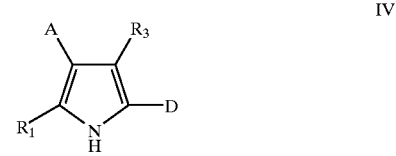

wherein A, $R_1$ and $R_3$ are as defined above; and

D is selected from the group consisting of —CHO, CN, —COR$_p$, —C(=O)OR$_p$, or R$_q$C(O)NH—, where R$_p$ and R$_q$ are each independently selected from H or substituted or unsubstituted C$_1$–C$_6$ alkyl, aryl or halogenated alkyl;

with chloramine, in the presence of a suitable base, to form a compound of Formula V:

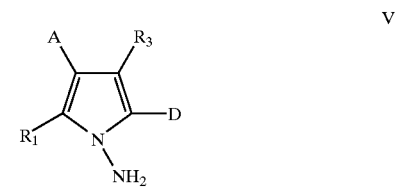

b) cyclizing the compound V to form a compound VI:

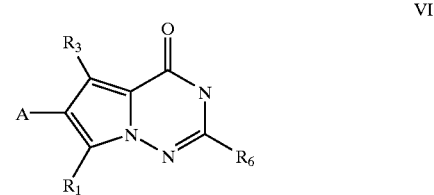

c) halogenating the compound VI to form a compound VII:

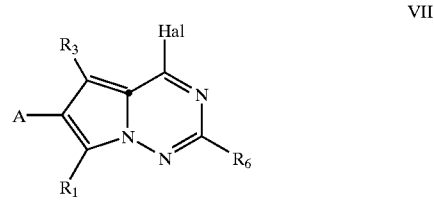

d) further reacting compound VII with a reactant B—ZR$_4$R$_5$, wherein Z, R$_4$ and R$_5$ are as defined above; and B is selected from H, substituted or unsubstituted alkyl, or substituted or unsubstituted cycloalkyl;

to form a compound of Formula I. Preferably, the reactant B—ZNR$_4$R$_5$ is of the formula VIII

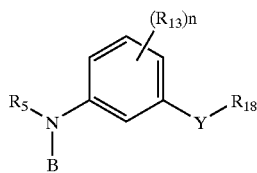

VIII wherein Y is selected from —C(=O)NR$_{23}$—, —NR$_{23}$C(=O)NR$_{23}$—, —NR$_{23}$SO$_2$—, or —SO$_2$NR$_{23}$;

R$_5$ is selected from hydrogen or alkyl; R$_{13}$ is selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, and aryloxy, and each R$_{13}$ may be further substituted by hydroxy, alkyl, alkoxy, aryl, or aralkyl, and n is an integer between 1 and 3;

R$_{18}$ and R$_{23}$ are each independently selected from hydrogen, alkyl, cycloalkyl, heterocyclo, alkoxy, aryl, and aryl/heterocyclo substituted with one to three R$_{19}$, except that when Y is —NR$_{23}$SO$_2$—, R$_{18}$ is C$_{1-4}$alkyl or aryl optionally substituted with one to three R$_{19}$; and R$_{13}$ and R$_{19}$ at each occurrence are independently selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, and aryloxy, wherein each R$_{13}$ and/or R$_{19}$ group may be further substituted by hydroxy, alkyl, alkoxy, aryl, or aralkyl. More preferably, the reactant of Formula VIII is:

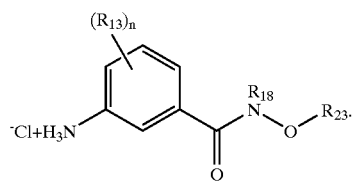

In another aspect, the invention comprises a compound according to formula V:

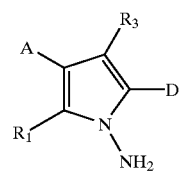

V wherein A, R$_3$, D and R$_1$ are as defined above.

In yet another aspect, the invention comprises a compound according to formula VI:

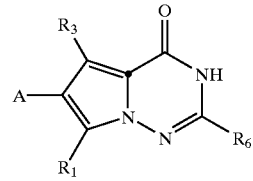

VI wherein A, R$_3$, D and R$_1$ are as defined above.

The invention further comprises a compound according to the formula VII:

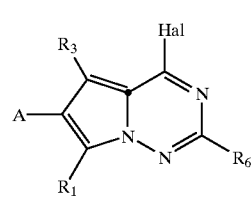

VII wherein A, R$_1$ and R$_3$ are as defined above.

In particular, the invention provides an improved method of preparing such compounds when compared to other methods involving amination of a readily available pyrrole starting reactant. The reaction using chloramine provides an aminated pyrrole in acceptable yields while avoiding the use of more hazardous aminating reagents. In contrast to the use of chloramine, for example, it has been found that aminating agents such as dinitro-substituted phenylhydroxylamines have been determined to be explosive, and to produce dinitrophenols, which are known toxic by-products (MSDS). Other aminating reagents such as hydroxylamine-O-sulfonic acid (HOSA), gave inferior yields (10–12%). Amination of pyrroles using oxaziridines also gave inferior results. Attempts at nitration of the desired pyrroles were also unsuccessful.

In certain preferred embodiments, the present invention is directed to a method of making pyrrolotriazine compounds of Formula (II):

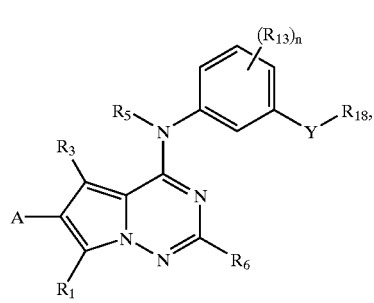

(II)

and pharmaceutically acceptable salts or solvates thereof, using the aforementioned procedure for compounds of formula I wherein:

R$_3$ is selected from H, alkyl, CF$_3$, O-alkyl, CN or NH$_2$;
R$_5$ is hydrogen or alkyl;
Y is selected from —C(=O)NR$_{23}$—, —NR$_{23}$C(=O)NR$_{23}$—, —NR$_{23}$SO$_2$—, or —SO$_2$NR$_{23}$—, or —NR$_{23}$C(O)O—;
R$_{18}$ and R$_{23}$ are selected from hydrogen, alkyl, cycloalkyl, heterocyclo, alkoxy, aryl, heteroaryl and aryl/heteroaryl substituted with one to three R$_{19}$, except when Y is —NR$_{23}$SO$_2$—, R$_{18}$ is C$_{1-4}$alkyl or aryl optionally substituted with one to three R$_{19}$;

R$_{13}$ and R$_{19}$ at each occurrence are independently selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, and aryloxy, wherein each R$_{13}$ and/or R$_{19}$ group may be further substituted by hydroxy, alkyl, alkoxy, aryl, or aralkyl; and A, R$_1$, and R$_6$ are as defined above for compounds of Formula (I).

Also included in the invention are the salts, solvates, and stereoisomers of the compounds of formula (II).

DETAILED DESCRIPTION OF PREFERRED EMBODIMENTS OF THE INVENTION

The invention comprises, in one aspect, a method of preparing pyrrolotriazine kinase inhibitors using a suitably substituted pyrrole as a starting material. According to certain preferred embodiments of the method, a pyrrole is reacted with a strong base, then aminated using a reactive haloamine, preferably chloramine. Suitably, this amination step is performed in a protic or aprotic solvent such as ether, MTBE, THF, toluene, water, DMF, NMPO, and DME, however other solvents may also be used. The resulting product can then be cyclized to form a pyrrolotriazine containing intermediate, which may optionally be further reacted to form the kinase inhibitors. It is also recognized that amination of the pyrrole can be used in applications other than cyclization to form pyrrolotriazines.

As used herein, the terms "cyclized" or "cyclizing" are intended to encompass any reactions that result in the formation of a 5- or 6-membered ring structure adjunctly connected to the pyrrole ring.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. The term "C$_{0-4}$alkyl" includes a bond and alkyl groups of 1 to 4 carbon atoms.

The term "substituted alkyl" refers to an alkyl group substituted by one to four substituents selected from halo, hydroxy, alkoxy, oxo (=O), alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. SO$_2$NH$_2$, substituted sulfonamido, nitro, cyano, carboxy, carbamyl, e.g. CONH$_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and substituted or unsubstituted heterocyclos, such as indolyl, imidazolyl, furyl, thienyl, thiazolyl, pyrrolidyl, pyridyl, pyrimidyl and the like. Where the substituent on the alkyl is further substituted, it will be with alkyl, alkoxy, aryl, or aralkyl.

When the term alkyl is used in connection with another group, as in heterocycloalkyl or cycloalkylalkyl, this means the identified group is bonded directly through an alkyl group which may be branched or straight chain. In the case of substituents, as in "substituted cycloalkylalkyl," the alkyl portion of the group may, besides being branched or straight chain, be substituted as recited above for substituted alkyl groups and/or the connected group may be substituted as recited herein for that group.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups. When the aryl is substituted, each ring of the aryl may be substituted.

The term "substituted aryl" refers to an aryl group substituted by one to four substituents selected from alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, and aryloxy. The substituent may be further substituted by hydroxy, alkyl, alkoxy, aryl, substituted aryl, substituted alkyl or aralkyl.

The term "aralkyl" refers to an aryl group bonded directly through an alkyl group, such as benzyl, wherein the alkyl group may be branched or straight chain. In the case of a "substituted aralkyl," the alkyl portion of the group may, besides being branched or straight chain, be substituted as recited above for substituted alkyl groups and/or the aryl portion may be substituted as recited for substituted aryl. Thus, the term "optionally substituted benzyl" refers to the group

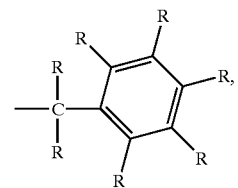

wherein each R group may be hydrogen or may also be selected from alkyl, halogen, cyano, nitro, amino, hydroxy, alkoxy, alkylthio, phenyl, benzyl, phenyloxy, and benzyloxy, and other groups recited above. At least two of these "R" groups should be hydrogen and preferably at least five of the "R" groups is hydrogen. A preferred benzyl group involves the alkyl-portion being branched to define

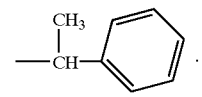

The term "heteroaryl" refers to an aromatic group for example, which is a 4 to 7 membered monocyclic, 7 to 11 membered bicyclic, or 10 to 15 membered tricyclic ring system, which has at least one heteroatom and at least one carbon atom-containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring.

A "substituted heteroaryl" has one to four substituents on any one or more of the rings comprising the heteraryl group. The substituents may be selected from those recited below for heterocycle groups.

Exemplary monocyclic heteroaryl groups include pyrrolyl, pyrazolyl, pyrazolinyl, imidazolyl, oxazolyl, isoxazolyl, thiazolyl (i.e.,

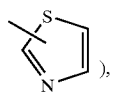

thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by one to two substituents selected from halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, and substituted and unsubstituted heterocycles, including indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by a substituent selected from halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and substituted or unsubstituted heterocyclo, e.g. imidazolyl, furyl, thienyl, thiazolyl, pyrrolidyl, pyridyl, pyrimidyl and the like.

The term "cycloalkyl" refers to a saturated or partially unsaturated non-aromatic cyclic hydrocarbon ring system, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. A "substituted cycloalkyl" is substituted at one or more ring positions with one or more alkyl or substituted alkyl groups as described above.

The terms "heterocycle", "heterocyclic" and "heterocyclo" each refer to a fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Thus, the term "heterocycle" includes heteroaryl groups as described above. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1, 3-dioxolane and tetrahydro-1, 1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Also included are smaller heterocycles, such as epoxides and aziridines.

Preferred heterocyclo groups include, without limitation:

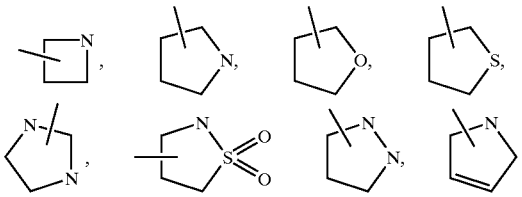

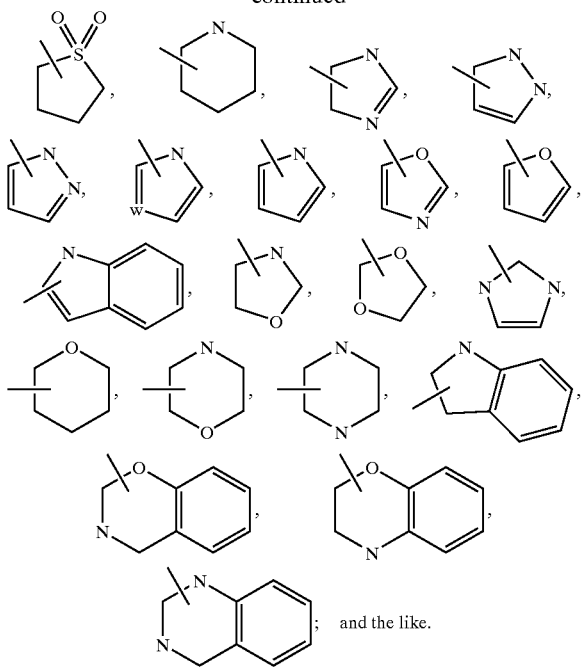

; and the like.

A "substituted heterocycle" will be substituted with one or more alkyl or aralkyl groups as described above, and/or one or more groups described above as alkyl substituents.

Unless otherwise indicated, when reference is made to a specifically-named heterocyclo or heteroaryl, the reference is intended to include those systems having the maximum number of non-cumulative double bonds or less than that maximum number of double bonds. Thus, for example, the term "isoquinoline" refers to isoquinoline and tetrahydroisoquinoline. The term "diazepine" refers to a heterocyclo ring having at least one seven atom ring with two nitrogen atoms in the seven membered ring, including a fully saturated or unsaturated diazepine.

The term "heteroatoms" shall include oxygen, sulfur and nitrogen.

The term "haloalkyl" means an alkyl having one or more halo substituents

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, substituted alkynyl, substituted aryl, substituted heterocycle, substituted cycloalkyl, and so forth, are as follows: alkoxy is —$OR^e$, alkanoyl is —$C(=O)R^e$, aryloxy is —OAr, alkanoyloxy is —$OC(=O)R^e$, amino is —$NH_2$, alkylamino is —$NHR^e$, arylamino is —NHAr, aralkylamino is —NH—$R^f$—Ar, disubstituted amine or dialkylamino is —$NR^gR^h$, alkanoylamino is —NH—C(=O)$R^e$, aroylamino is —NH—C(=O)Ar, aralkanoylamino is —NH—C(=O)$R^f$—Ar, thiol is —SH, alkylthio is —$SR^e$, arylthio is —SAr, aralkylthio is —S—$R^f$—Ar, alkylthiono is —S(=O)$R^e$, arylthiono is —S(=O)Ar, aralkylthiono is —S(=O)$R^f$—Ar, alkylsulfonyl is —$SO_{(k)}R^e$, arylsulfonyl is —$SO_{(k)}$Ar, arylsulfonylamine is —$NHSO_{(k)}$Ar, alkylsulfonylamine is —$NHSO_2R^e$, aralkylsulfonyl is —$SO_{(k)}R^f$Ar, sulfonamido is —$SO_2NH_2$, nitro is —$NO_2$, carboxy is —$CO_2H$, carbamyl is —$CONH_2$, substituted carbamyl is —C(=O)$NHR^g$ or —C(=O)$NR^gR^h$, alkoxycarbonyl is —C(=O)$OR^e$, carboxyalkyl is —$R^f$—$CO_2H$, sulfonic acid is —$SO_3H$, arylsulfonylamine is —$NHSO_{(k)}$Ar, guanidino is

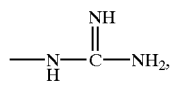

and ureido is

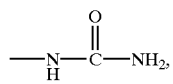

wherein $R^e$ is alkyl as defined above, $R^f$ is alkylene as defined above, $R^g$ and $R^h$ are selected from alkyl, aryl, and aralkyl, Ar is an aryl as defined above, and k is 2 or 3.

Throughout the specification, groups and substituents thereof may be chosen by one skilled in the field to provide stable moieties and compounds.

According to the invention, a selected pyrrole compound, which may be substituted or unsubstituted at the ring positions, is aminated using a haloamine, preferably chloramine, in the presence of a base, to form an aminated pyrrole with an active amino (—$NH_2$) group bonded to the ring nitrogen atom. The reactive species so formed may then be cyclized using heat (from about 100° C. to about 200° C., and preferably from about 120° C. to about 190° C.) and an appropriate catalyst, for example an acid, to provide an oxo-pyrrolotriazine-containing compound. The oxo-pyrrolotriazine formed according to the preferred embodiment of this invention may then be reacted with a halogenating agent, for example $POCl_3$, followed by a nucleophilic displacement to form a desired addition product of Formula (I).

The compounds of Formula (I) may form salts that are also within the scope of this invention. Pharmaceutically acceptable (i.e. non-toxic, physiologically acceptable) salts are preferred, although other salts are also useful, e.g., in isolating or purifying the compounds of this invention. All references to compounds of Formula (I) herein are intended to include without limitation compounds of Formulae (Ia) to (Ii) as well as compounds of Formula (II) and (IIa)–(IIh). All references to compounds of Formula (II) are intended to include compounds of Formulae (IIa) to (IIh).

The compounds of Formula (I) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds of Formula (I) may be reacted with a variety of organic and inorganic acids to form salts. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

The processes of the invention can be used to produce all stereoisomers of the compounds of Formula I, either in a racemic mixture or in pure or substantially pure form. Additionally, the definition of the compounds herein embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should further be understood that solvates (e.g., hydrates) of the compounds of Formula (I) are also with the scope of the present invention. Methods of solvation are generally known in the art.

Preferred embodiments of the invention include the methods for preparing the preferred compounds of Formula (Ia):

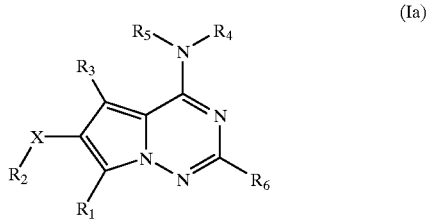

(Ia)

and pharmaceutically acceptable salts, prodrugs, or solvates thereof, comprising reacting a pyrrole of formula IV wherein:

$R_1$ is selected from hydrogen, —$CH_3$, —OH, —$OCH_3$, —SH, —$SCH_3$, —OC(=O)$R_{21}$, —S(=O)$R_{22}$, —$SO_2R_{22}$, —$SO_2NR_{24}R_{25}$, —$CO_2R_{21}$, —C(=O)NR$_{24}$R$_{25}$, —NH$_2$, —NR$_{21}$SO$_2$NR$_{24}$R$_{25}$, —NR$_{21}$SO$_2$R$_{22}$, —NR$_{24}$C(=O)R$_{25}$, —NR$_{24}$CO$_2$R$_{25}$, —NR$_2$C(=O)NR$_{24}$R$_{25}$, halogen, nitro, or cyano;

$R_3$ is selected from H, $C_1$-$C_6$ alkyl, OH, —$CF_3$, —$OCF_3$, CN or $NH_2$;

X is selected from —C(=O)—, —$CO_2$—, —O—, —NR$_{10}$C(=O)—, and —C(=O)NR$_{10}$—, or X is absent;

$R_2$ is selected from hydrogen, $C_{2-6}$alkyl, substituted $C_{1-4}$alkyl, aryl, aralkyl, substituted aryl, substituted aralkyl, cycloalkyl, substituted cycloalkyl, heterocycle, or substituted heterocycle, or optionally-substituted cycloalkylalkyl or heterocycloalkyl;

$R_4$ is selected from aryl or heteroaryl substituted with one $R_{12}$ and zero to three $R_{13}$;

$R_5$ and $R_{10}$ independently are selected from hydrogen and lower alkyl; $R_6$ is selected from hydrogen, alkyl, substituted alkyl, aryl, substituted aryl, heterocyclo, substituted heterocyclo, —NR$_7$R$_8$, —OR$_7$, or halogen;

$R_{12}$ is selected from carbamyl, sulfonamido, arylsulfonylamine, or ureido, each of which is optionally substituted with up to two of hydroxy, alkyl, substituted alkyl, alkoxy, aryl, substituted aryl, and aralkyl, or $R_{12}$ is alkylsulfonylamine;

$R_{13}$ at each occurrence is independently selected from alkyl, substituted alkyl, halo, trifluoromethoxy, trifluoromethyl, —OR$_{14}$, —C(=O)alkyl, —OC(=O)alkyl, —NR$_{15}$R$_{16}$, —SR$_{15}$, —NO$_2$, —CN, —CO$_2$R$_{15}$, —CONH$_2$, —SO$_3$H, —S(=O)alkyl, —S(=O)aryl, —NHSO$_2$-aryl-R$_{17}$, —NHSO$_2$-alkyl, —SO$_2$NHR$_{17}$, —CONHR$_{17}$, and —NHC(=O)NHR$_{17}$;

$R_{14}$ is selected from hydrogen, alkyl, or aryl;

$R_{15}$ is hydrogen or alkyl;

$R_{16}$ is hydrogen, alkyl, aralkyl, or alkanoyl;

$R_{17}$ is hydrogen, hydroxy, alkyl, substituted alkyl, alkoxy, aryl, substituted aryl, or aralkyl;

$R_7$, $R_8$, $R_{10}$, $R_{11}$, $R_{21}$, $R_{24}$, and $R_{25}$ are independently selected from hydrogen and alkyl; and $R_{22}$ is alkyl or substituted alkyl.

Certain preferred compounds of Formula (Ia) that may be prepared according to the methods of the invention are those in which $R_3$ is $C_1$-$C_6$ alkyl, trifluoromethyl, or methoxy, most preferably methyl; X is preferably —CO$_2$—, —NR$_{10}$C(=O)—, or —C(=O)NR$_{10}$—, more preferably —C(=O)NH—; Z is preferably N; $R_4$ is preferably substituted aryl or substituted heteroaryl, more preferably phenyl substituted with at least one of carbamyl, substituted carbamyl, arylsulfonylamido, substituted arylsulfonylamido, ureido, or substituted ureido, and optionally substituted with one or two $C_{1-4}$alkyl or halogen. Most preferably $R_4$ is phenyl substituted with at least one of —C(=O)NHO($C_{1-4}$alkyl) or —C(=O)NH(optionally substituted phenyl), and also is optionally substituted with $C_{1-4}$alkyl. $R_5$ is preferably hydrogen or lower alkyl, more preferably hydrogen.

Additionally, in these preferred embodiments, $R_1$ and $R_6$ may be selected from groups of substituents as defined herein; however, advantageously they are selected from hydrogen, $CH_3$, —OH, —$OCH_3$, halogen, nitro, and cyano, and most preferably $R_1$ and $R_6$ are hydrogen. $R_2$ preferably is alkyl, aryl, substituted aryl, aralkyl, substituted aralkyl, heteroaryl, or substituted heteroaryl, more preferably straight or branched $C_2$-$C_6$ alkyl or optionally-substituted benzyl. The mesylate salt is the preferred form of salt.

Further, the methods of the invention further comprise those for making preferred compounds of the Formula (II),

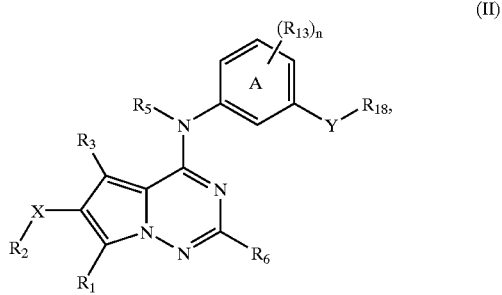

(II)

and pharmaceutically acceptable salts or solvates thereof, wherein:

$R_3$ is selected from H, $C_1$-$C_6$ alkyl, OH, —$CF_3$, —$OCF_3$, CN or $NH_2$;

X is selected from —C(=O)NR$_{10}$—, —NR$_{10}$ C(=O)—, —C(=O)—, or —CO$_2$—;

Y is selected from —C(=O)NH—, —NHC(=O)NH—, or —NHSO$_2$—;

$R_{10}$ is hydrogen or lower alkyl;

$R_{18}$ is selected from hydrogen, alkyl, cycloalkyl, alkoxy, aryl, and aryl substituted with one to three $R_{19}$, except that when Y is —NHSO$_2$—, R$_{18}$ is —C$_{1-4}$alkyl, aryl or aryl substituted with R$_{19}$;

R$_{13}$ is attached to any available carbon atom of phenyl ring A and at each occurrence is independently selected from alkyl, substituted alkyl, halo, trifluoromethoxy, trifluoromethyl, —OR$_{14}$, —C(=O)alkyl, —OC(=O)alkyl, —NR$_{15}$R$_{16}$, —SR$_{15}$, —NO$_2$, —CN, —CO$_2$R$_{15}$, —CONH$_2$, —SO$_3$H, —S(=O)alkyl, —S(=O)aryl, —NHSO$_2$-aryl-R$_{17}$, —SO$_2$NHR$_{17}$, —CONHR$_{17}$, and —NHC(=O)NHR$_{17}$;

R$_{14}$, R$_{15}$, R$_{16}$ and R$_{17}$ are independently selected from hydrogen or alkyl;

R$_{19}$ at each occurrence is selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, and aryloxy, wherein each group R$_{19}$ may be further substituted by hydroxy, alkyl, alkoxy, aryl, or aralkyl;

n is 0, 1 or 2, and

R$_1$, R$_2$ and R$_6$ are as defined above for compounds of Formula (I).

The invention may also be practiced in the synthesis of preferred compounds according to the Formulae (IIa) or (IIb):

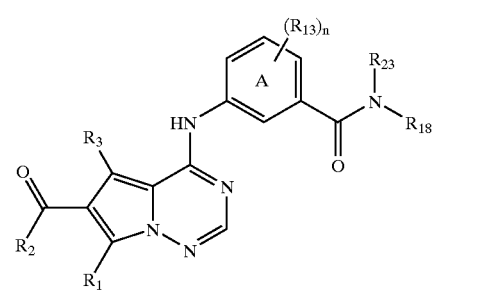

(IIa)

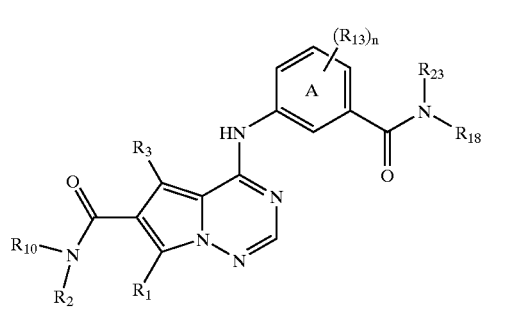

(IIb)

and pharmaceutically acceptable salts, prodrugs, or solvates thereof, wherein:

R$_3$ is selected from H, C$_1$–C$_6$ alkyl, alkoxy, OH, —CF$_3$, —OCF$_3$, CN or NH$_2$;

R$_1$ and R$_{10}$ are each either hydrogen or —CH$_3$;

R$_2$ is selected from hydrogen; straight or branched C$_{2-6}$alkyl; cycloalkyl optionally substituted with keto and/or up to two R$_{27}$; phenyl optionally substituted with up to two R$_{27}$; heterocycle optionally substituted with keto and/or up to two R$_{27}$; and C$_{1-4}$alkyl substituted with up to three of halogen, trifluoromethyl, cyano, OR$_{28}$, NR$_{28}$R$_{29}$, CO$_2$R$_{28}$, aryl, heterocycle, and/or cycloalkyl, wherein the aryl, heterocycle, and/or cycloalkyl in turn are optionally substituted with up to two of halogen, hydroxy, alkoxy, haloalkyl, haloalkoxy, nitro, cyano and alkyl; R$_{18}$ is selected from hydroxy, C$_{1-4}$alkoxy, phenyl, or phenyl substituted with one or two R$_{19}$;

R$_{13}$ and R$_{19}$ are independently selected from lower alkyl, halogen, trifluoromethoxy, trifluoromethyl, hydroxy, C$_{1-4}$alkoxy, nitro, and cyano;

R$_{27}$ at each occurrence is independently selected from hydrogen, alkyl, trifluoromethyl, trifluoromethoxy, halogen, cyano, nitro, amino, hydroxy, alkoxy, phenyl, benzyl, phenyloxy, and benzyloxy;

R$_{28}$ and R$_{29}$ at each occurrence are independently selected from hydrogen, alkyl, alkenyl, phenyl, and benzyl; and n is 0, 1 or 2.

When R$_2$ is a heterocyclo, advantageously it is selected from diazepinyl, morpholinyl, piperidinyl, and pyrrolidinyl, said heterocycle being optionally substituted with C$_{1-4}$alkyl, phenyl, and/or benzyl.

The methods of the invention are also preferably used for making compounds having the formula (III):

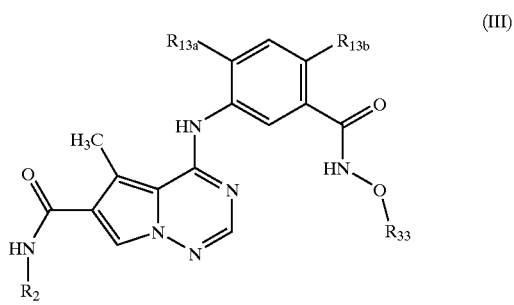

(III)

in which R$_{13a}$ and R$_{13b}$ are hydrogen, CH$_3$, OH, OCH$_3$, CF$_3$, cyano, or halogen, R$_2$ is C$_{2-6}$alkyl or optionally substituted benzyl, R$_{33}$ is lower alkyl.

The compounds prepared according to the invention are known kinase inhibitors. Compounds of Formula (I) are useful in treating kinase-associated conditions including, but not limited to, inflammatory diseases, oncology diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS<ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

Abbreviations

For ease of reference, the following abbreviations are employed herein, including the methods of preparation and Examples that follow:
Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DCM=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-1-yl-N,N,N',N'-tetramethyluronim hexafluorophosphate
KOH=potassium hydroxide
$K_2CO_3$=potassium carbonate
$POCl_3$=phosphorous oxychloride
KOtBu=potassium t-butoxide
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
$Na_2S_2O_3$=sodium thiosulfate
Pd=palladium
Pd/C=palladium on carbon
min=minute(s)
L=liter
mL=milliliter
µL=microliter
g=gram(s)
mg=milligram(s)
mol=moles
mmol=millimole(s)
meq=milliequivalent
RT or rt=room temperature
ret. t.=HPLC retention time (minutes)
sat or sat'd=saturated
aq.=aqueous
TLC=thin layer chromatography
HPLC=high performance liquid chromatography
RP HPLC=reverse phase HPLC
LC/MS=high performance liquid chromatography/mass spectrometry
MS=mass spectrometry
NMR=nuclear magnetic resonance
mp=melting point In the Examples, "HPLC Condition A" refers to YMC S5 ODS 4.6×50 mm Ballistic column, 4 mL/min flow rate, 4 min linear gradient elution (Start solvent % B=0; Final solvent % B=100), solvent A=10% MeOH/90% $H_2O$/0.2% $H_3PO_4$.

The processes of the invention and other previously disclosed processes are disclosed in the following schemes. In the schemes, the groups $R_1$–$R_6$, $R_{10}$, $R_{13}$, $R_{18}$, $R_{23}$, X and Z are as described herein for compounds of Formula (I).

Scheme 1

A pyrrole (1) can be reacted with KOtBu, NaH, or other strong base, in a suitable solvent such as ether, THF, DMF, water, toluene, NMPO or DME. Subsequent addition of a haloamine such as chloranine affords the aminated pyrrole (2). Cyclization using an appropriate agent such as formamide at elevated temperature (e.g. about 120–190° C.) affords the oxopyrrolotriazine (3).

Scheme 2

21

-continued

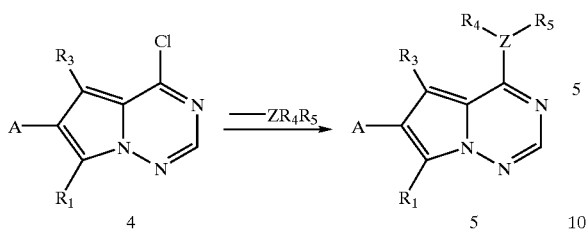

Oxopyrrolotriazine (3) can be reacted with a suitable chlorinating agent, such as $POCl_3$, in a suitable solvent such as toluene, to afford chloropyrrolotriazine (4). Reaction of the chloropyrrolotriazine with a suitable substituted nucleophile affords pyrrolotriazine (5).

Scheme 3

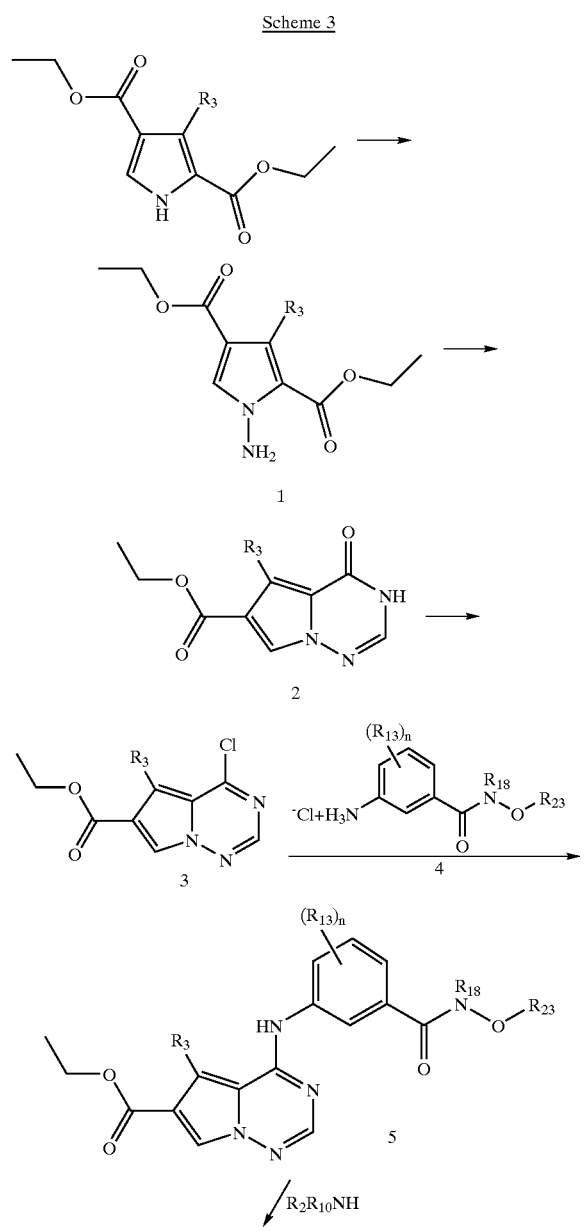

22

-continued

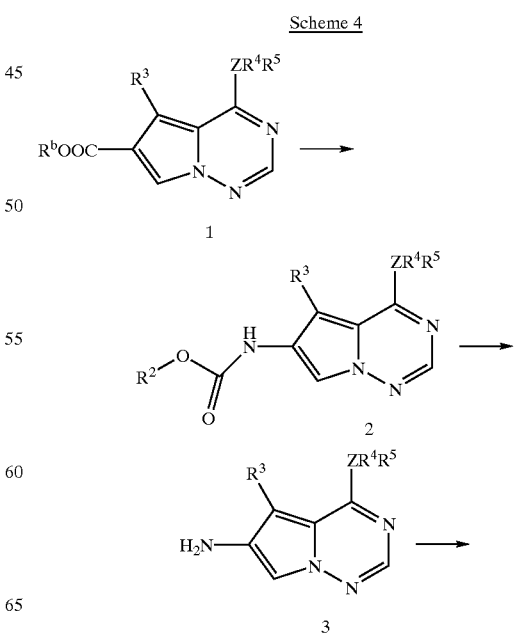

An ester such as 3-methyl-1-pyrrole-2,4-diethyl ester can be reacted with chloramine in an appropriate solvent to produce compound (1). Reacting compound (1) in formamide with acetic acid produces compound (2). Compound (2) can be reacted with DIPEA and $POCl_3$ in toluene to produce compound (3). Compound (3) can be reacted with DIPEA and compound (4) in DMF to produce compound (5). Compound (5) can be reacted in THF with NaOH to produce an acid intermediate which upon treatment with HOBt, EDCI and the appropriate amine ($NR_2R_{10}$) in DMF produces compounds (6).

Compound (4) can be prepared by 1) reacting commercially-available 4-amino-3-methylbenzoic acid and N-(tert-butoxycarbonyl)anhydride in THF to produce a BOC-protected aniline intermediate; 2) reacting the aniline intermediate with -(3-dimethylaminopropyl)-3-ethylcarbodiimide hydrochloride, HOBt, and DMF, followed by addition of methoxyamine hydrochloride and DIPEA to produce a BOC-protected N-methoxyamide intermediate; and 3) reacting that methoxyamide intermediate in a solution of HCl in dioxane to produce compound (4) as a hydrochloride salt. Alternatively, compound (4) can be prepared as shown in Scheme 6.

Scheme 4

-continued

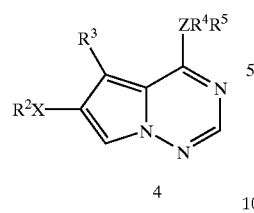

wherein X=NR$^{10}$, NR$^{10}$CO, NR$^{10}$CONR$^{11}$, NR$^{10}$COO, NR$^{10}$SO$_2$, NR$^{10}$SO$_2$NR$^{11}$, as described hereinbefore.

Compound (1) where $R^b$ is a carbon-containing substituent can be converted to carboxylic acid (1), where $R^b$ is H, and wherein R$_3$ is alkyl or alkoxy or is as otherwise defined herein, by treatment with a base such as aq. KOH. This acid undergoes Curtis rearrangement by treatment with diphenyl phosphoryl azide in the presence of an alcohol, such as benzyl alcohol, in an organic solvent, such as 1,4-dioxane, to afford compound (2).

The carbamate group of compound (2) can be deprotected, when optionally protected by groups such as CBZ, by hydrogenation over a catalyst, such as Pd, to obtain compound (3). The amino group of compound (3) can be acylated to form compound (4), e.g., by treatment with a carboxylic acid in the presence of a coupling agent such as DCC, or sulfonylated, e.g., by treatment with a sulfonyl chloride. Alternatively, the amino group of compound (3) may be alkylated with alkyl halides or may undergo reductive amination with aldehydes in the presence of a reducing agent, such as sodium cyanoborohydride.

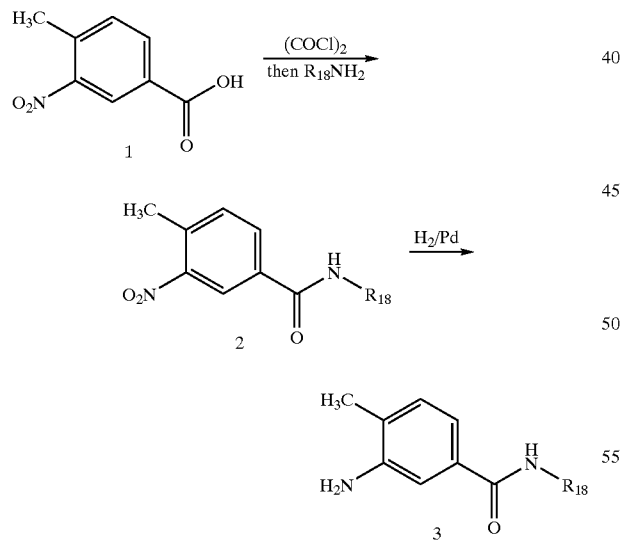

Commercially-available compound (1) can be reacted with oxalyl chloride with heating and then concentrated in vacuo and reacted with an amine R$_{18}$NH$_2$ in the presence of a base, such as diisopropylethylamine, in an organic solvent, such as DCM to yield compound (2). Compound (2) can be reacted with hydrogen in the presence of a catalyst, such as Pd, in an alcoholic solvent, such as EtOH, at rt to afford compound (3). Compound (3) can then be used as in Scheme 3 to produce compounds (6) of Scheme 3.

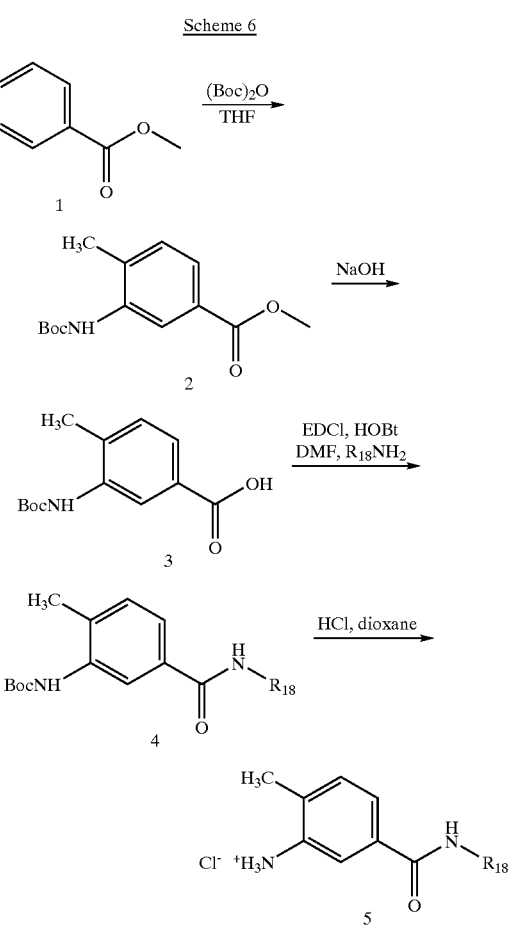

Alternatively, commercially-available compound (1) can be reacted with di-tert-butyl dicarbonate in an organic solvent, such as THF, to afford compound (2). Compound (2) can be hydrolyzed using an aqueous base, such as sodium hydroxide, to afford compound (3) that can be reacted with an amine R$_{18}$NH$_2$ in the presence of coupling reagents, such as EDCI and HOBt, in an organic solvent, such as DMF, to afford compound (4). Compound (4) can then be reacted with HCl in a solvent, such as dioxane, to afford compound (5). Compound (5) can also be used as in Scheme 3 to produce compounds (6) of Scheme 3.

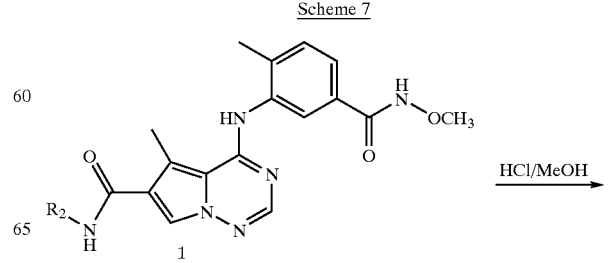

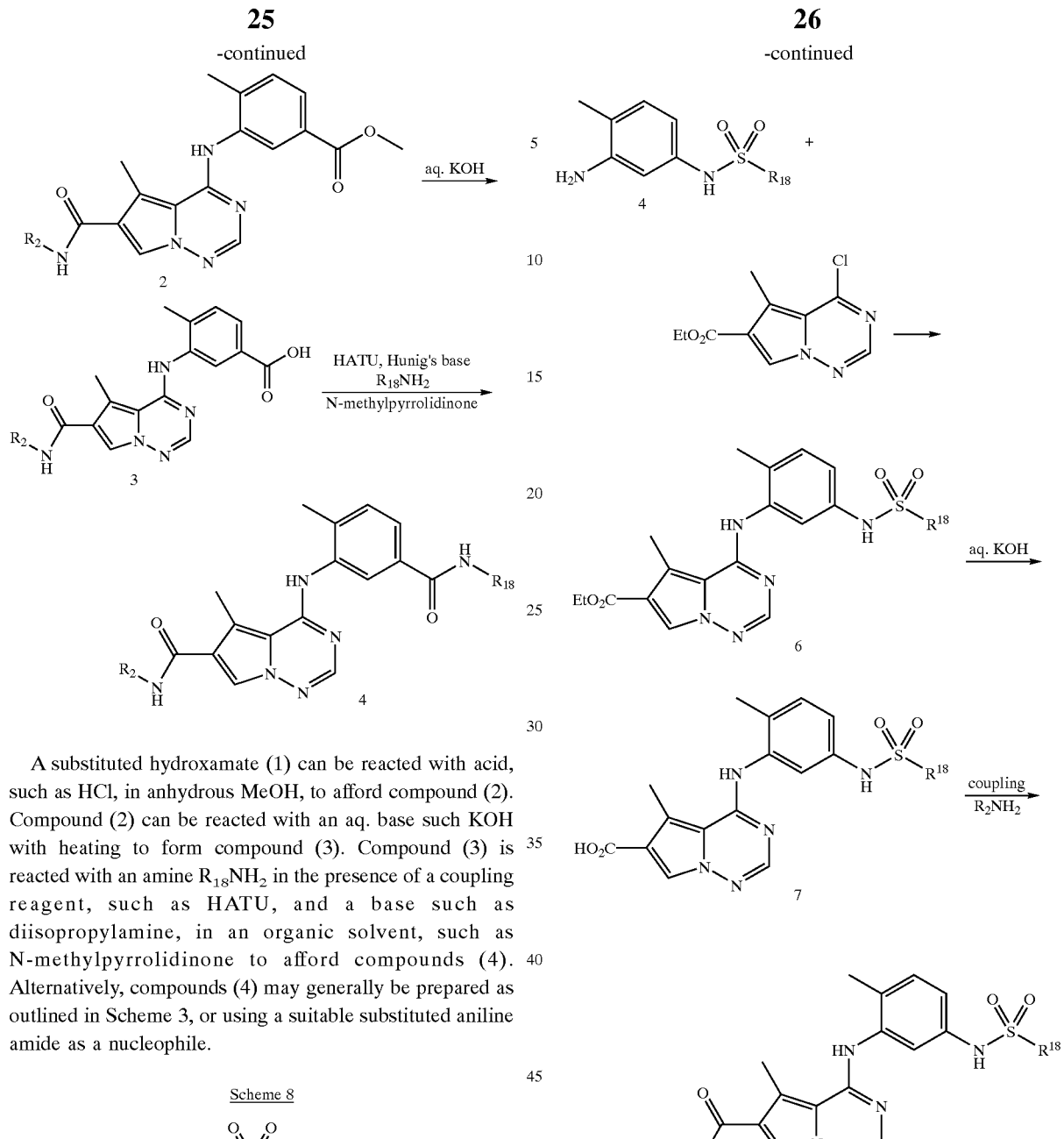

A substituted hydroxamate (1) can be reacted with acid, such as HCl, in anhydrous MeOH, to afford compound (2). Compound (2) can be reacted with an aq. base such KOH with heating to form compound (3). Compound (3) is reacted with an amine $R_{18}NH_2$ in the presence of a coupling reagent, such as HATU, and a base such as diisopropylamine, in an organic solvent, such as N-methylpyrrolidinone to afford compounds (4). Alternatively, compounds (4) may generally be prepared as outlined in Scheme 3, or using a suitable substituted aniline amide as a nucleophile.

Scheme 8

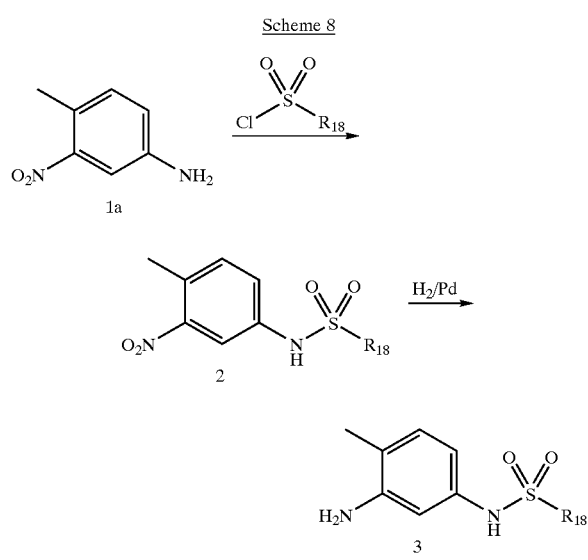

Commercially-available compound (1a) can be reacted with a sulfonyl chloride in the presence of a base, such as TEA, in an organic solvent, such as DCM to yield compound (2). Reaction of compound (2) with hydrogen in the presence of a catalyst, such as Pd in a solvent, such as MeOH, yields compound (3). Reaction of compound (3) with chloride (5) (compound 3 of scheme 3) in an organic solvent, such as DMF, at rt affords compound (6).

Reaction of compound (6) with aq. KOH with heating affords compound (7). Compound (7) can be reacted with an amine $R_2NH_2$ in the presence of a coupling reagent, such as EDCI, and a base such as diisopropylamine, in an organic solvent, such as DMF to afford compound (8).

Scheme 9

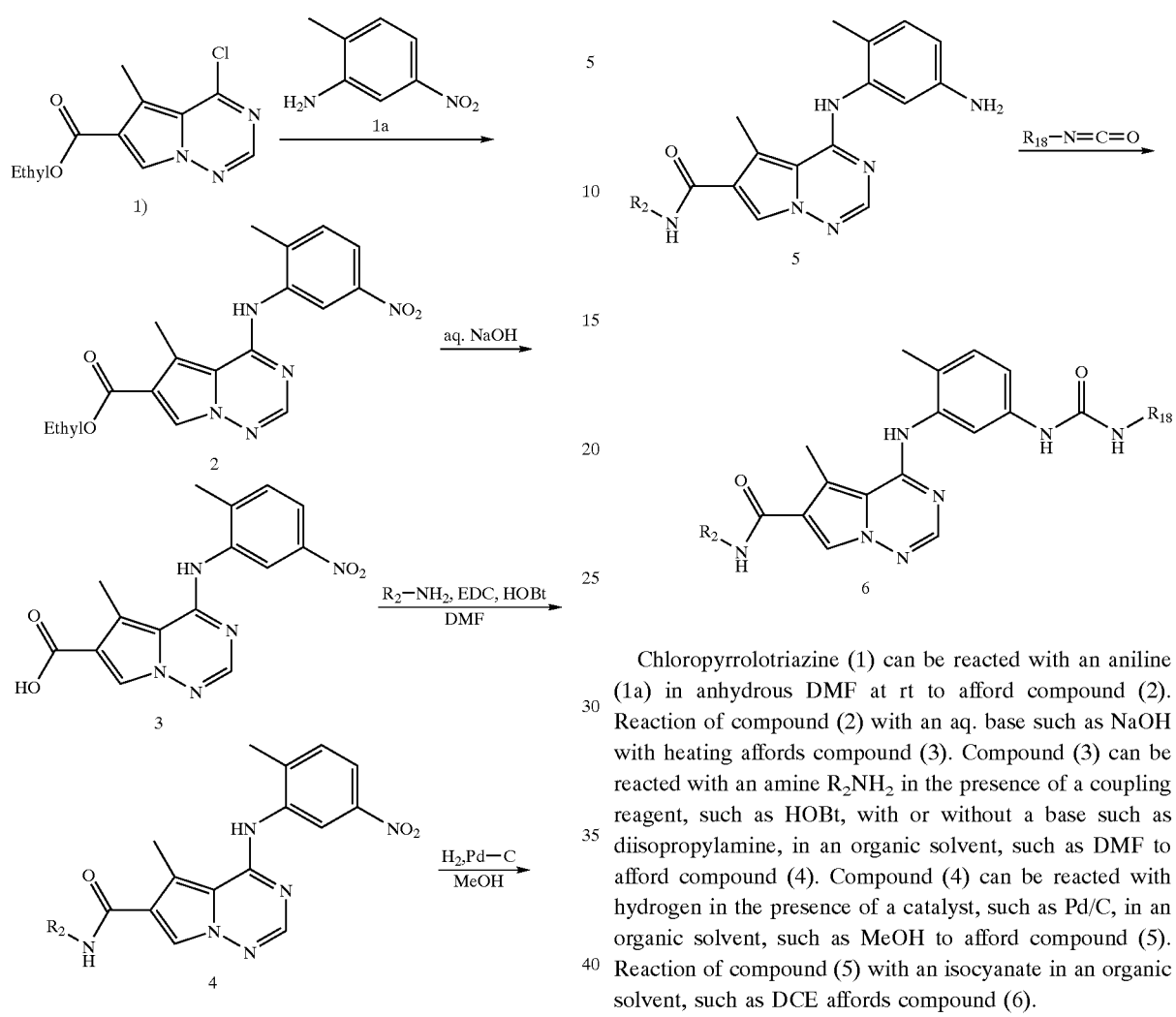

Chloropyrrolotriazine (1) can be reacted with an aniline (1a) in anhydrous DMF at rt to afford compound (2). Reaction of compound (2) with an aq. base such as NaOH with heating affords compound (3). Compound (3) can be reacted with an amine $R_2NH_2$ in the presence of a coupling reagent, such as HOBt, with or without a base such as diisopropylamine, in an organic solvent, such as DMF to afford compound (4). Compound (4) can be reacted with hydrogen in the presence of a catalyst, such as Pd/C, in an organic solvent, such as MeOH to afford compound (5). Reaction of compound (5) with an isocyanate in an organic solvent, such as DCE affords compound (6).

Scheme 10

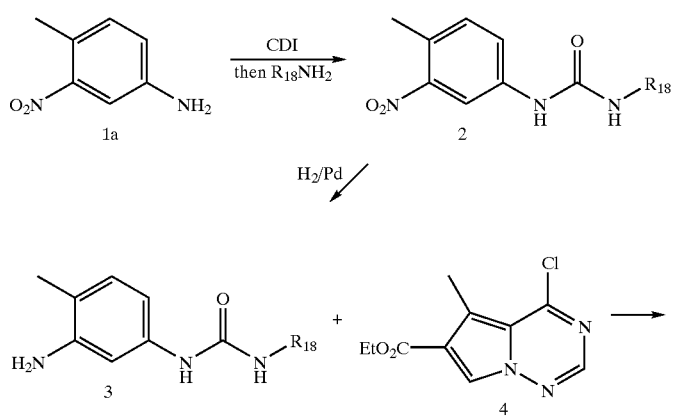

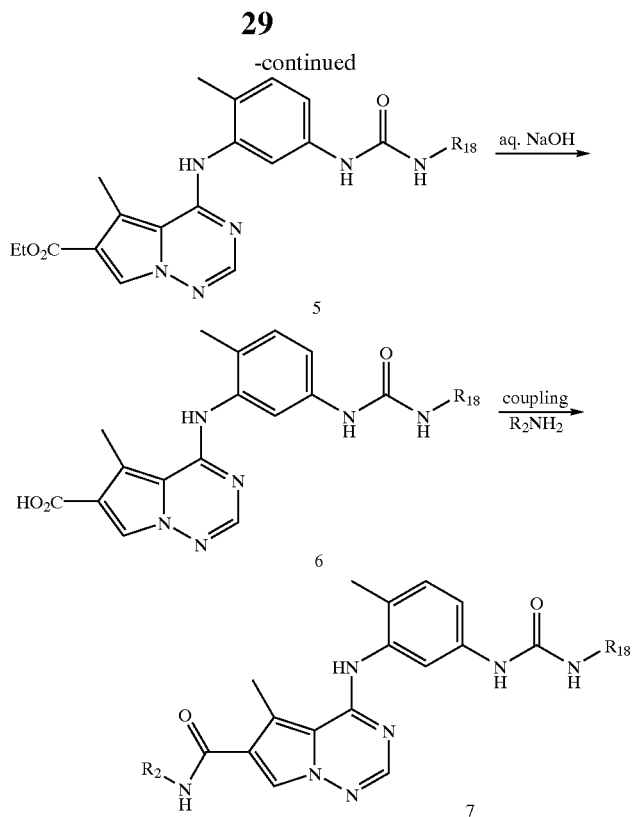

Commercially-available compound (1a) (compound 1a of Scheme 8), can be reacted with carbonyl diimidazole and with an amine $R_{18}NH_2$ in an organic solvent, such as DCE, to yield compound (2). Reaction of compound (2) with hydrogen in the presence of a catalyst, such as Pd, in an alcoholic solvent such as EtOH affords compound (3). Reaction of (3) with chloride (4) in an organic solvent, such as DMF, affords compound (5). Reaction of (5) with aq. NaOH with heating affords product (6). Product (6) can be reacted with an amine $R_2NH_2$ in the presence of a coupling reagent, such as EDCI, and a base such as diisopropylamine, in an organic solvent, such as DMF to afford compound (7).

EXAMPLE 1

N-Cyclopropyl-4-[[5-[(methoxyamino)carbonyl]-2-methylphenyl]amino]-5-methylpyrrolo[2,1-f][1,2,4]triazine-6-carboxamide

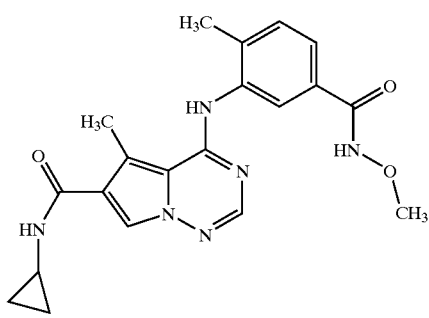

The compound of Example 1 was prepared as set forth below, using the Scheme 3 described above, wherein Compounds (A)-(E) have the structures indicated below.

A.

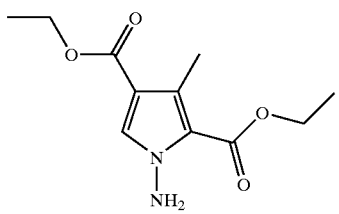

To a solution of the 3-methyl-1-pyrrole-2,4-diethyl ester (100 mg) (J. *Heterocyclic Chem* Vol. 34 (1997), at pp. 177–193; *Heterocycles*, Vol. 50 (1999), at pp. 853–866; *Synthesis* (1999), at pp. 479–482). Generally, the synthesis of pyrroles is described by the commonly assigned patent documents referenced herein and the procedure of M. Suzuki, M. Miyoshi, and K. Matsumoto *J. Org. Chem*. 1974, 39 (1980)) in DMF (0.44M) was added either NaH or KOtBu (1.2 equiv.) at rt. This solution was stirred for 30–45 minutes. Chloramine in ether (ca. 0.15 sM, 1 eq.) was added via syringe. The solution was stirred for 1.5 h or until starting material was converted to product as judged by HPLC analysis. The reaction was then quenched with aq. $Na_2S_2O_3$ and extracted with EtOAc or $Et_2O$. The organic extracts were washed with water and brine and then dried over sodium sulfate. Compound A was obtained in >90% yield. $NH_2Cl$ in ether was prepared according to the procedure of Nunn, *J. Chem. Soc. (C)*, (1971) at p. 823.

B.

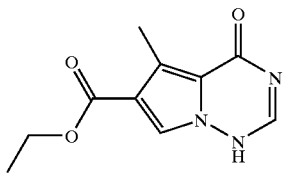

To a solution of Compound A (2 g) in formamide (8 mL) was added acetic acid (20% by weight), and the mixture was heated at 120° C. for 24 h. The reaction mixture was cooled and water added (32 mL) to precipitate the product. The solids were collected by filtration and washed with EtOAc to furnish Compound B as a yellow solid (90%).

C.

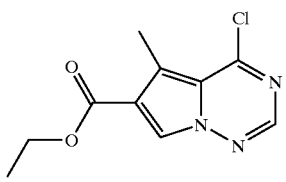

To a solution of Compound B (10 g, 45.2 mmol) in toluene (150 mL) was added DIPEA (6.31 mL, 36.2 mmol, 0.8 equiv.) and POCl$_3$ (5.05 mL, 54.2 mmol, 1.2 equiv.) and the reaction mixture heated at 120–125° C. (oil bath temp) for 20 h. The reaction mixture was cooled and poured into ice cold sat. NaHCO$_3$-water-toluene (450 mL-450 mL-150 mL) and stirred rapidly to assure quenching of the excess POCl$_3$. The layers were separated (filtered through celite if a suspension forms) and the organic layer was washed again with sat. NaHCO$_3$. The organic layer was dried over Na$_2$SO$_4$, filtered and concentrated in vacuo to afford Compound C as a tan yellow solid (9.9 g, 95%).

D

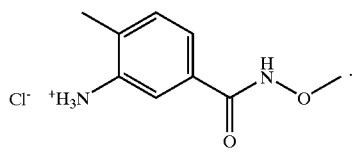

A mixture of commercially-available 4-amino-3-methylbenzoic acid (100 g, 0.66 mol) and N-(tert-butoxycarbonyl)anhydride (150 g, 0.68 mol) in THF (1000 mL) was slowly heated to 50° C. overnight. The resulting mixture was cooled to rt and the solvent was removed on a rotary evaporator. The resulting solids were triturated with hexanes and dried in vacuo to afford 151 g (91%) of the crude BOC-protected aniline intermediate as a light pink solid.

To the above, light-pink solid was added EDCI (127 g, 0.66 mol), HOBt (90 g, 0.66 mol), and DMF (1000 ml), and the resulting mixture was stirred at rt for 30 minutes followed by addition of methoxyamine hydrochloride (55 g, 0.66 mol) in one portion. After stirring for 10 min, the mixture was cooled using an ice bath. DIPEA (250 ml, 1.4 mol) was added at such a rate so as to maintain the internal reaction temperature below 25° C. After the addition was complete, the ice bath was removed and the reaction was stirred overnight at rt. The reaction mixture was partitioned between 0.5 L of water and 1.5 L of EtOAc and the resulting layers were separated. The aqueous portion was extracted with additional EtOAc (400 mL×3), and the combined organic extracts were washed with water (300 mL×3), cold 0.5 N aq. HCl (400 mL×2), and water (500 mL). The product was then extracted with cold 0.5 N aq. NaOH (300 mL×3) and the combined basic aqueous extracts were neutralized to pH=8 by a slow addition of cold 0.5 N aq. HCl. The resulting solid which precipitated was collected by filtration and washed with cold water. The wet solid was decolorized in hot EtOH with active charcoal to give 106 g of white solid as the BOC-protected N-methoxyamide intermediate.

To a slurry of the above solid (91 g, 0.32 mol) in 1,4-dioxane (400 mL) at rt was added a 4M solution of HCl in dioxane (400 mL), and the resulting mixture was stirred at rt overnight. Diethyl ether (1000 mL) was added and the precipitated solid was collected by filtration and triturated with a hot EtOH/H$_2$O mixture (4:1 v/v). Drying the resulting solid in vacuo afforded 53 g of the pure hydrochloride salt (Compound D) as a white solid. $_1$H NMR (d$_6$-DMSO): δ 9.5–9.9 (br. s, 1H), 7.75 (s, 1H), 7.55 (d, 1H), 7.36 (d, 1H), 3.70 (s, 3H), 2.38 (s, 3H).

E

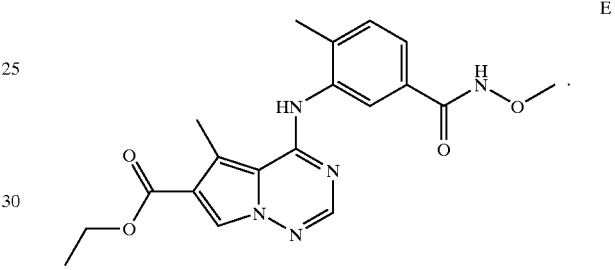

To a solution of the Compound D (41.2 g, 190 mmol) in DMF (230 ML) was added DIPEA (33.1 mL, 180.7 mmol, 0.95 equiv.), and the reaction vessel was heated to 55° C. (oil bath temp). Solid Compound C (45.6 g, 190 mmol) was added in several portions over 10 minutes and the flask was rinsed with DMF (150 mL) and added to the reaction. The reaction was heated for 10 hours at 55° C. and cooled to rt. The mixture was then poured into 1.5 L water diluted to 2.2 L with ice slowly over 10 minutes. The pH was adjusted to 6 and the solids were stirred for 1 h. The solids were filtered, washed with water (2×200 mL) and dried on the filter to give 71.9 g crude ester. The solid was then suspended in acetonitrile (450 mL) and heated with stirring at 50° C. for 1 h. The mixture was cooled and filtered to give 64.2 g product (>99% purity). These solids were then dissolved in hot EtOH (2.8 L) and decolorizing carbon (6.4 g) was added followed by heating at reflux for 15 min. The mixture was then filtered through a pad of celite and the reaction flask rinsed with hot EtOH (1 L). The hot filtrate was then concentrated to ~1 L of EtOH by distillation upon which the product started to crystallize out of solution at a volume of 2.5 L. The solution was cooled and placed in a cold room with stirring for 40 h. The solids were filtered and rinsed with 1/1 EtOH/Et$_2$O (500 mL) to give 58.5 g of Compound E as a white solid (80%).

F. To a solution of ester Compound E (22.5 g, 58.7 mmol) in THF (205 mL) was added 1 N NaOH (205 mL) and the reaction mixture heated to 50° C. for 16 h. The THF was removed in vacuo and the mixture was acidified to pH 4–5 with 1N aq. HCl to precipitate the product. The heterogeneous mixture was stirred for 1 h, filtered and washed with water (150 mL) and ether (150 mL). The collected solids were partially dried on the filter to give the crude acid intermediate as a moist white solid which was used without further purification.

To a solution of the moist acid in 300 mL of DMF was added HOBt (11.9 g, 88.0 mmol), EDCI (16.9 g, 88.0 mmol) and 1.3 equivalents (117 mmol) of cyclopropyl-amine as the free base or as the hydrochloride salt. The mixture was stirred for 30 min to solubilize the solids, placed in a cold water bath, and DIPEA (20.4 mL, 117 mmol) was added slowly via syringe. The reaction mixture was allowed to stir at rt for 1 h, then poured into rapidly stirred ice water (1.2 L) to precipitate the product. After stirring for 3 h, the solids were collected by suction filtration, washed with water (150 mL) and ether (2×100 mL), and allowed to air dry by suction filtration to give Example 2 (92–98%) as a white solid.

Alternatively, commercially-available compound (1b), as shown in Scheme 6 above, can be reacted with di-tert-butyl dicarbonate in an organic solvent, such as THF, to afford compound (5) of Scheme 6. This compound (5) can also be used as in Scheme 3 to produce compounds (6) of Scheme 4.

EXAMPLES 2–55

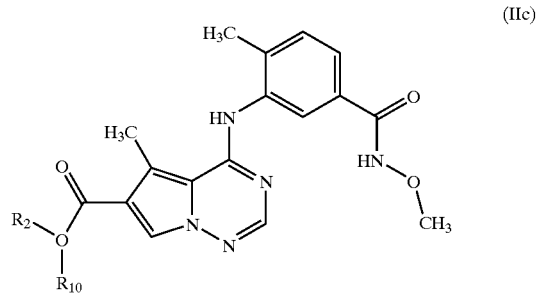

(IIc)

Compounds having the formula (IIc), wherein $R_2$ and $R_{10}$ have the values listed in Table 1 were prepared following the same methods set forth above in Scheme 3 and Example 1, using different amines ($NR_2R_{10}$) in the last step. Additionally, each compound can be recrystallized using a 7 to 1 EtOH/water mixture to afford analytically pure product as a white crystalline solid.

TABLE 1

| Ex. | $R_2$ | $R_{10}$ | Compound Name | Data MS/HPLC |
|---|---|---|---|---|
| 2 | —CH$_2$—C(CH$_3$)$_3$ | CH$_3$ | N-(2,2-Dimethylpropyl)-4-[[5-[(methoxyamino)carbonyl]-2-methylphenyl]amino]-N,5-dimethylpyrrolo[2,1-f][1,2,4]triazine-6-carboxamide | 439.3 3.43 min |
| 3 | —CH—(CH$_3$)$_2$ | H | 4-[[5-[(Methoxyamino)carbonyl]-2-methylphenyl]amino]-5-methyl-N-(1-methylethyl)pyrrolo[2,1-f][1,2,4]triazine-6-carboxamide | 397.3 2.79 min |
| 4 | —CH$_2$—CH(CH$_3$)(CH$_3$) | H | 4-[[5-[(Methoxyamino)carbonyl]-2-methylphenyl]amino]-5-methyl-N-(2-methylpropyl)pyrrolo[2,1-f][1,2,4]triazine-6-carboxamide | 411.4 3.14 min |
| 5 | —CH$_2$—C(CH$_3$)$_3$ | H | N-(2,2-Dimethylpropyl)-4-[[5-[(methoxyamino)Carbonyl]-2-methylphenyl]amino]-5-methylpyrrolo[2,1-f][1,2,4]triazine-6-carboxamide | 425.3 3.35 min |
| 6 | —(CH$_2$)$_2$—CH$_3$ | H | 4-[[5-[(Methoxyamino)carbonyl]-2-methylphenyl]amino]-5-methyl-N-propylpyrrolo[2,1-f][1,2,4]triazine-6-carboxamide | 397.2 2.88 min |
| 7 | —C(CH$_3$)$_3$ | H | N-(1,1-Dimethylethyl)-4-[[5-[(methoxyamino)carbonyl]-2-methylphenyl]amino]-5-methylpyrrolo[2,1-f][1,2,4]triazine-6-carboxamide | 411.2 3.11 min |
| 8 | —(CH$_2$)$_2$—OCH$_3$ | H | 4-[[5-[(Methoxyamino)carbonyl]-2-methylphenyl]amino]-N-(2-methoxyethyl)-5-methylpyrrolo[2,1-f][1,2,4]triazine-6-carboxamide | 413.2 1.99 min |
| 9 | cyclohexyl | H | N-Cyclohexyl-4-[[5-[(methoxyamino)carbonyl]-2-methylphenyl]amino]-5-methylpyrrolo[2,1-f][1,2,4]triazine-6-carboxamide | 437.4 2.88 min |
| 10 | —CH(CH$_3$)(phenyl) | H | 4-[[5-[(Methoxyamino)carbonyl]-2-methylphenyl]amino]-5-methyl-N-[(1R)-1-phenylethyl]pyrrolo[2,1-f][1,2,4]triazine-6-carboxamide | 459.3 2.85 min |

TABLE 1-continued

| Ex. | R$_2$ | R$_{10}$ | Compound Name | Data MS/HPLC |
|---|---|---|---|---|
| 11 | -CH(CH$_3$)-phenyl (1S) | H | 4-[[5-[(Methoxyamino)carbonyl]-2-methylphenyl]amino]-5-methyl-N-[(1S)-1-phenylethyl]pyrrolo[2,1-f][1,2,4]triazine-6-carboxamide | 459.3 2.85 min |
| 12 | -CH$_2$-(4-fluorophenyl) | H | N-[(4-Fluorophenyl)methyl]-4-[[5-[(methoxyamino)carbonyl]-2-methylphenyl]amino]-5-methylpyrrolo[2,1-f][1,2,4]triazine-6-carboxamide | 463.4 2.83 min |
| 13 | -CH$_2$-(2-methoxyphenyl) | H | 4-[[5-[(Methoxyamino)carbonyl]-2-methylphenyl]amino]-N-[(2-methoxyphenyl)methyl]-5-methylpyrrolo[2,1-f][1,2,4]triazine-6-carboxamide | 475.4 2.83 min |
| 14 | -CH$_2$-(4-pyridinyl) | H | 4-[[5-[(Methoxyamino)carbonyl]-2-methylphenyl]amino]-5-methyl-N-(4-pyridinylmethyl)pyrrolo[2,1-f][1,2,4]triazine-6-carboxamide | 446.2 1.45 min |
| 15 | -(CH$_2$)$_2$-(4-pyridinyl) | H | 4-[[5-[(Methoxyamino)carbonyl]-2-methylphenyl]amino]-5-methyl-N-[2-(4-pyridinyl)ethyl]pyrrolo[2,1-f][1,2,4]triazine-6-carboxamide | 460.3 1.81 min |
| 16 | -(CH$_2$)$_2$-(1-piperidinyl) | H | 4-[[5-[(Methoxyamino)carbonyl]-2-methylphenyl]amino]-5-methyl-N-[2-(1-piperidinyl)ethyl]pyrrolo[2,1-f][1,2,4]triazine-6-carboxamide | 466.4 1.56 min |
| 17 | -(CH$_2$)$_2$-(4-morpholinyl) | H | 4-[[5-[(Methoxyamino)carbonyl]-2-methylphenyl]amino]-5-methyl-N-[2-(4-morpholinyl)ethyl]pyrrolo[2,1-f][1,2,4]triazine-6-carboxamide | 468.3 1.38 min |
| 18 | (1R,2S)-2-hydroxy-1-methyl-2,3-dihydro-1H-inden-1-yl | H | N-[(1R, 2S)-2,3-Dihydro-1H-inden-1-yl]-4-[[5-[(methoxyamino)carbonyl]-2-methylphenyl]amino]-5-methylpyrrolo[2,1-f][1,2,4]triazine-6-carboxamide | 487.4 2.74 min |
| 19 | (1S,2R)-2-hydroxy-2,3-dihydro-1H-inden-1-yl | H | N-[(1S, 2R)-2,3-Dihydro-1H-inden-1-yl]-4-[[5-[(methoxyamino)carbonyl]-2-methylphenyl]amino]-5-methylpyrrolo[2,1-f][1,2,4]triazine-6-carboxamide | 487.2 2.74 min |
| 20 | cyclopropyl | H | N-Cyclopropyl-4-[[5-[(methoxyamino)carbonyl]-2-methylphenyl]amino]-5-methylpyrrolo[2,1-f][1,2,4]triazine-6-carboxamide | 395.3 2.64 min |
| 21 | cyclopentyl | H | N-Cyclopentyl-4-[[5-[(methoxyamino)carbonyl]-2-methylphenyl]amino]-5-methylpyrrolo[2,1-f][1,2,4]triazine-6-carboxamide | 423.0 3.15 min |

TABLE 1-continued

| Ex. | R$_2$ | R$_{10}$ | Compound Name | Data MS/HPLC |
|---|---|---|---|---|
| 22 | 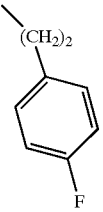 —(CH$_2$)$_2$—(4-F-C$_6$H$_4$) | H | N-[2-(4-Fluorophenyl)ethyl]-4-[[5-[(methoxyamino)carbonyl]-2-methylphenyl]amino]-5-methylpyrrolo[2,1-f][1,2,4]triazine-6-carboxamide | 477.3 3.53 min |
| 23 | 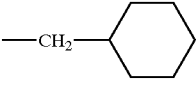 —CH$_2$—cyclohexyl | H | N-(Cyclohexylmethyl)-4-[[5-[(methoxyamino)carbonyl]-2-methylphenyl]amino]-5-methylpyrrolo[2,1-f][1,2,4]triazine-6-carboxamide | 451.3 3.70 min |
| 24 | 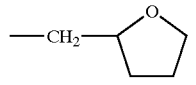 —CH$_2$-(tetrahydrofuran-2-yl) | H | 4-[[5-[(Methoxyamino)carbonyl]-2-methylphenyl]amino]-5-methyl-N-[(tetrahydro-2-furanyl)methyl]pyrrolo[2,1-f][1,2,4]triazine-6-carboxamide | 439.3 2.76 min |
| 25 | 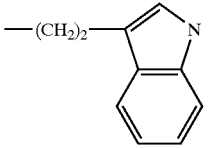 —(CH$_2$)$_2$-(indol-3-yl) | H | N-(2-1H-Indol-3-ylethyl)-4-[[5-[(methoxyamino)carbonyl]-2-methylphenyl]amino]-5-methylpyrrolo[2,1-f][1,2,4]triazine-6-carboxamide | 498.3 3.39 min |
| 26 | —(CH$_2$)$_3$—CH$_3$ | H | N-Butyl-4-[[5-[(methoxyamino)carbonyl]-2-methylphenyl]amino]-5-methylpyrrolo[2,1-f][1,2,4]triazine-6-carboxamide | 411.2 3.16 min |
| 27 | 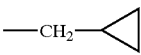 —CH$_2$-cyclopropyl | H | N-(Cyclopropylmethyl)-4-[[5-[(methoxyamino)carbonyl]-2-methylphenyl]amino]-5-methylpyrrolo[2,1-f][1,2,4]triazine-6-carboxamide | 409.1 2.90 min |
| 28 | 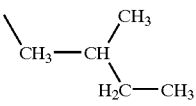 2-methylbutyl | H | 4-[[5-[(Methoxyamino)carbonyl]-2-methylphenyl]amino]-5-methyl-N-(2-methylbutyl)pyrrolo[2,1-f][1,2,4]triazine-6-carboxamide | 425.3 3.43 min |
| 29 | 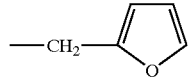 —CH$_2$-(furan-2-yl) | H | N-(2-Furanylmethyl)-4-[[5-[(methoxyamino)carbonyl]-2-methylphenyl]amino]-5-methylpyrrolo[2,1-f][1,2,4]triazine-6-carboxamide | 435.1 2.95 min |
| 30 | 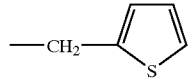 —CH$_2$-(thiophen-2-yl) | H | 4-[[5-[(Methoxyamino)carbonyl]-2-methylphenyl]amino]-5-methyl-N-(2-thienylmethyl)pyrrolo[2,1-f][1,2,4]triazine-6-carboxamide | 451.2 3.16 min |
| 31 | 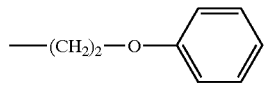 —(CH$_2$)$_2$—O—C$_6$H$_5$ | H | 4-[[5-[(Methoxyamino)carbonyl]-2-methylphenyl]amino]-5-methyl-N-(2-phenoxyethyl)pyrrolo[2,1-f][1,2,4]triazine-6-carboxamide | 475.3 3.43 min |
| 32 | 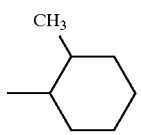 2-methylcyclohexyl | H | 4-[[5-[(Methoxyamino)carbonyl]-2-methylphenyl]amino]-5-methyl-N-(2-methylcyclohexyl)pyrrolo[2,1-f][1,2,4]triazine-6-carboxamide | 451.2 3.56 min |
| 33 | —CH$_2$—CH$_3$ | CH$_3$ | N-Ethyl-4-[[5-[(methoxyamino)carbonyl]-2-methylphenyl]amino]-N,5-dimethylpyrrolo[2,1-f][1,2,4]triazine-6-carboxamide | 397.2 2.59 min |

TABLE 1-continued

| Ex. | R$_2$ | R$_{10}$ | Compound Name | Data MS/HPLC |
|---|---|---|---|---|
| 34 | —CH$_2$—CF$_3$ | H | 4-[[5-[(Methoxyamino)carbonyl]-2-methylphenyl]amino]-5-methyl-N-(2,2,2-trifluoroethyl)pyrrolo[2,1-f][1,2,4]triazine-6-carboxamide | 437.1 3.01 min |
| 35 | —CH$_2$—CH$_2$—F | H | N-(2-Fluoroethyl)-4-[[5-[(methoxyamino)carbonyl]-2-methylphenyl]amino]-5-methylpyrrolo[2,1-f][1,2,4]triazine-6-carboxamide | 401.2 2.44 min |
| 36 | 2,3-dihydro-1H-inden-2-yl | H | N-(2,3-Dihydro-1H-inden-2-yl)-4-[[5-[(methoxyamino)carbonyl]-2-methylphenyl]amino]-5-methylpyrrolo[2,1-f][1,2,4]triazine-6-carboxamide | 471.2 3.56 min |
| 37 | —CH$_2$—CH$_3$ | H | N-Ethyl-4-[[5-[(methoxyamino)carbonyl]-2-methylphenyl]amino]-5-methylpyrrolo[2,1-f][1,2,4]triazine-6-carboxamide | 383.3 2.58 min |
| 38 | H$_2$C—CF$_2$—CF$_3$ | H | 4-[[5-[(Methoxyamino)carbonyl]-2-methylphenyl]amino]-5-methyl-N-(2,2,3,3,3-pentafluoropropyl)pyrrolo[2,1-f][1,2,4]triazine-6-carboxamide | 487.2 3.40 min |
| 39 | —(CH$_2$)$_2$—N(CH$_3$)$_2$ | H | 4-[[5-[(Methoxyamino)carbonyl]-2-methylphenyl]amino]-5,7-dimethyl-N-(1-methylethyl)pyrrolo[2,1-f][1,2,4]triazine-6-carboxamide | 426.5 1.38 min |
| 40 | 4-fluorophenyl | H | N-(4-Fluorophenyl)-4-[[5-[(methoxyamino)carbonyl]-2-methylphenyl]amino]-5-methylpyrrolo[2,1-f][1,2,4]triazine-6-carboxamide | 449.2 2.92 min |
| 41 | 2-methoxyphenyl | H | 4-[[5-[(Methoxyamino)carbonyl]-2-methylphenyl]amino]-N-(2-methoxyphenyl)-5-methylpyrrolo[2,1-f][1,2,4]triazine-6-carboxamide | 461.2 2.97 min |
| 42 | (3-methoxyphenyl)methyl | H | 4-[[5-[(Methoxyamino)carbonyl]-2-methylphenyl]amino]-N-[(3-methoxyphenyl)methyl]-5-methylpyrrolo[2,1-f][1,2,4]triazine-6-carboxamide | 475.4 2.75 min |
| 43 | 3-(trifluoromethyl)phenyl | H | 4-[[5-[(Methoxyamino)carbonyl]-2-methylphenyl]amino]-5-methyl-N-[3-(trifluoromethyl)phenyl]pyrrolo[2,1-f][1,2,4]triazine-6-carboxamide | 499.1 3.39 min |
| 44 | —CH$_2$-(2,6-dichlorophenyl) | H | N-[(2,6-Dichlorophenyl)methyl]-4-[[5-[(methoxyamino)carbonyl]-2-methylphenyl]amino]-5-methylpyrrolo[2,1-f][1,2,4]triazine-6-carboxamide | 513.1 3.10 min |

TABLE 1-continued

| Ex. | R$_2$ | R$_{10}$ | Compound Name | Data MS/HPLC |
|---|---|---|---|---|
| 45 | —CH(C≡N)—CH$_2$—phenyl | H | N-[(1S)-1-Cyano-2-phenylethyl]-4-[[5-[(methoxyamino)carbonyl]-2-methylphenyl]amino]-5-methylpyrrolo[2,1-f][1,2,4]triazine-6-carboxamide | 484.3 2.88 min |
| 46 | —(CH$_2$)$_2$—phenyl | H | 4-[[5-[(Methoxyamino)carbonyl]-2-methylphenyl]amino]-5-methyl-N-(2-phenylethyl)pyrrolo[2,1-f][1,2,4]triazine-6-carboxamide | 459.3 2.91 min |
| 47 | —CH$_2$-(2-pyridinyl) | H | 4-[[5-[(Methoxyamino)carbonyl]-2-methylphenyl]amino]-5-methyl-N-(2-pyridinylmethyl)pyrrolo[2,1-f][1,2,4]triazine-6-carboxamide | 446.2 1.51 min |
| 48 | —CH$_2$-phenyl | H | 4-[[5-[(Methoxyamino)carbonyl]-2-methylphenyl]amino]-5-methyl-N-(phenylmethyl)pyrrolo[2,1-f][1,2,4]triazine-6-carboxamide | 445.2 2.69 min |
| 49 | 2-methyl-4-methylthiazol-yl | H | 4-[[5-[(Methoxyamino)carbonyl]-2-methylphenyl]amino]-5-methyl-N-(4-methyl-2-thiazolyl)pyrrolo[2,1-f][1,2,4]triazine-6-carboxamide | 452.3 3.50 min |
| 50 | —CH(CH$_3$)—CH$_2$—CH$_3$ (1R) | H | 4-[[5-[(Methoxyamino)carbonyl]-2-methylphenyl]amino]-5-methyl-N-[(1R)-1-methylpropyl]pyrrolo[2,1-f][1,2,4]triazine-6-carboxamide | 411.2 3.20 min |
| 51 | —CH(CH$_3$)—CH$_2$—CH$_3$ (1S) | H | 4-[[5-[(Methoxyamino)carbonyl]-2-methylphenyl]amino]-5-methyl-N-[(1S)-1-methylpropyl]pyrrolo[2,1-f][1,2,4]triazine-6-carboxamide | 411.2 3.20 min |
| 52 | —CH$_2$-(3-fluorophenyl) | H | N-[(3-Fluorophenyl)methyl]-4-[[5-[(methoxyamino)carbonyl]-2-methylphenyl]amino]-5-methylpyrrolo[2,1-f][1,2,4]triazine-6-carboxamide | 463.2 2.84 min |
| 53 | —CH(CH$_3$)-(4-fluorophenyl) | H | N-[1-(4-Fluorophenyl)ethyl]-4-[[5-[(methoxyamino)carbonyl]-2-methylphenyl]amino]-5-methylpyrrolo[2,1-f][1,2,4]triazine-6-carboxamide | 477.3 2.93 min |
| 54 | —CH$_2$-(2,4-difluorophenyl) | H | N-[(2,4-Difluorophenyl)methyl]-4-[[5-[(methoxyamino)carbonyl]-2-methylphenyl]amino]-5-methylpyrrolo[2,1-f][1,2,4]triazine-6-carboxamide | 481.2 2.92 min |

TABLE 1-continued

| Ex. | R₂ | R₁₀ | Compound Name | Data MS/HPLC |
|---|---|---|---|---|
| 55 | 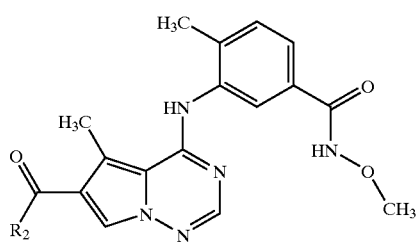 | H | N-[(2,6-Difluorophenyl)methyl]-4-[[5-[(methoxyamino)carbonyl]-2-methylphenyl]amino]-5-methylpyrrolo[2,1-f][1,2,4]triazine-6-carboxamide | 481.1 2.70 min |

EXAMPLES 56–59

(IId)

EXAMPLES 60–64

(IIe)

Compounds having the formula (IId), wherein the R₂ groups have the values listed in Table 2, were prepared following the same methods set forth above in Scheme 3 and Examples 2–55.

Compounds having the formula (IIe), wherein X and R₂ have the values listed in table 3, were prepared following the same or similar procedure as in Scheme 3 and Example 1, except in the first step, commercially available 3-trifluoromethyl-1-pyrrole-2,4-diethyl ester was used instead of 3-methyl-1-pyrrole-2,4-diethyl ester.

TABLE 2

| Ex. | R₂ | Compound Name | Data |
|---|---|---|---|
| 56 | 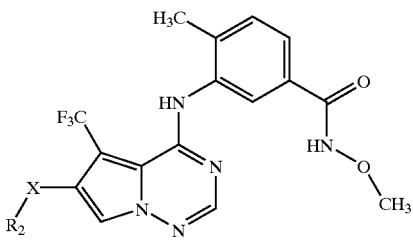 | 3-[[6-[(Hexahydro-4-methyl-1H-1,4-diazepin-1-yl)carbonyl]-5-methyl pyrrolo[2,1-f][1,2,4]triazin-4-yl]amino]-N-methoxy-4-methylbenzamide | 452.1 1.63 min |
| 57 | | N-Methoxy-4-methyl-3-[[5-methyl-6-(4-morpholinylcarbonyl) pyrrolo[2,1-f][1,2,4]triazin-4-yl]amino]benzamide | 425.2 1.82 min |
| 58 | | N-Methoxy-4-methyl-3-[[5-methyl-6-[[4-(phenylmethyl)-1-piperidinyl]carbonyl] pyrrolo[2,1-f][1,2,4]triazin-4-yl]amino]benzamide | 513.4 3.45 min |
| 59 | | N-Methoxy-4-methyl-3-[[5-methyl-6-(1-pyrrolidinylcarbonyl) pyrrolo[2,1-f][1,2,4]triazin-4-yl]amino]benzamide | 409.2 2.16 min |

TABLE 3

| Ex. No. | X | R₂ | Compound Name | Data MS/HPLC |
|---|---|---|---|---|
| 60 | O=C(O–)–  (ester linkage) | —CH₂—CH₃ | 4-[[5-[(Methoxyamino)carbonyl]-2-methylphenyl]amino]-5-(trifluoromethyl)pyrrolo[2,1-f][1,2,4]triazine-6-carboxylic acid ethyl ester | 438.2 3.76 min |
| 61 | O=C(HN–)– | —CH₂—CH₃ | N-Ethyl-4-[[5-[(methoxyamino)carbonyl]-2-methylphenyl]amino]-5-(trifluoromethyl)pyrrolo[2,1-f][1,2,4]triazine-6-carboxamide | 437.2 2.99 min |
| 62 | O=C(HN–)– | —CH₂—CH₂—CH₃ | 4-[[5-[(Methoxyamino)carbonyl]-2-methylphenyl]amino]-N-propyl-5-(trifluoromethyl)pyrrolo[2,1-f][1,2,4]triazine-6-carboxamide | 451.3 3.21 min |
| 63 | O=C(HN–)– | —CH(CH₃)—CH₂—CH₃ | 4-[[5-[(Methoxyamino)carbonyl]-2-methylphenyl]amino]-N-[(1S)-1-methylpropyl]-5-(trifluoromethyl)pyrrolo[2,1-f][1,2,4]triazine-6-carboxamide | 465.3 3.36 min |
| 64 | O=C(HN–)– | —CH(CH₃)(C₆H₅) | 4-[[5-[(Methoxyamino)carbonyl]-2-methylphenyl]amino]-N-[(1S)-1-phenylethyl]-5-(trifluoromethyl)pyrrolo[2,1-f][1,2,4]triazine-6-carboxamide | 513.2 1.72 min |

EXAMPLE 65

N-Ethyl-4-[[5-[(methoxyamino)carbonyl]-2-methylphenyl]amino]-5-methylpyrrolo[2,1-f][1,2,4]triazine-6-carboxamide Methane Sulfonic Acid

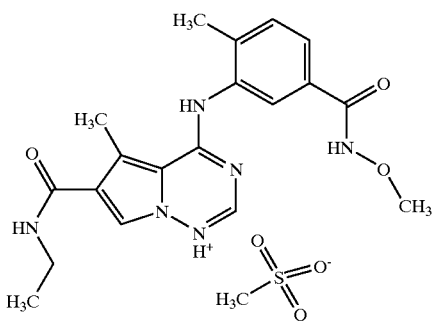

Example 37 as a free base was charged with acetone (10 ml/g), and the jacket was heated to 50–60° C. Reflux was started at 55–57° C., and the mixture was stirred for 30 min. at 50–60° C. Methanesulfonic acid (1.2 eq.) was added, and a slight exotherm was observed. The slurry was stirred at 50–60° C. until DSC showed in two consecutive samples the complete conversion of the free base (mp 220–222° C.) to the mesylate salt (mp 259–261° C.). The slurry was cooled to 20–25° C. over about 30 min, and then stirred for at least 30 min. with the temp. kept at 20–25° C. The slurry was then filtered, washed with acetone, and dried in vacuo at 40–50° C. to an LOD<0.5% to provide Example 65 as a white crystalline solid (yield 90–95%). [M+H]⁺=478.4. The above procedure may be used to prepare mesylate salts of other compounds of Formulae (I) and (II) herein.

EXAMPLES 66–69

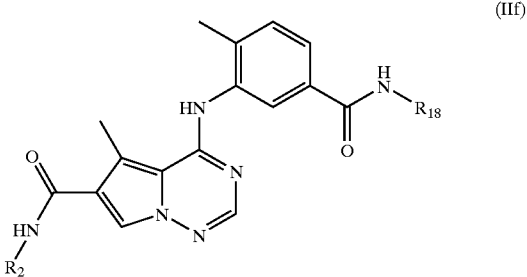

(IIf)

Compounds of Formula (IIf) were prepared using appropriate substrates and amines selected to afford compounds where $R_2$ and $R_{18}$ have the values listed in Table 4.

TABLE 4

| Ex. | R₂ | R₁₈ | Compound Name | Data |
|---|---|---|---|---|
| 66 | Et | (3-trifluoromethylphenyl)-NH-C(=O)- | N-Ethyl-5-methyl-4-[[2-methyl-5-[[[3-(trifluoromethyl)phenyl]amino]carbonyl]phenyl]amino]pyrrolo[2,1-f][1,2,4]triazine-6-carboxamide | $^1$H NMR (CD$_3$OD w/TFA): δ 8.28 (s, 1H), 8.19 (s, 1H), 8.16 (d, 1H), 8.11 (d, 1H), 7.84 (s, 1H), 7.71 (d, 1H), 7.58 (t, 2H), 7.47 (d, 1H), 3.44 (q, 2H), 2.94 (s, 3H), 2.47 (s, 3H), 1.26 (t, 3H). LCMS (M + H$^+$) = 497.47. HPLC (Condition A): 3.30 min. |
| 67 | Et | 4-cyanophenyl | 4-[[5-[[(4-Cyanophenyl)amino]carbonyl]-2-methylphenyl]amino]-N-ethyl-5-methyl pyrrolo[2,1-f][1,2,4] triazine-6-carboxamide | $^1$H NMR (CD$_3$OD): δ 7.93 (br s, 1H), 7.84–7.86 (d, 3H), 7.74 (d, 1H), 7.62 (d, 2H), 7.58 (s, 1H), 7.40 (d, 1H), 3.30 (q, 2H), 3.21 (s, 3H), 2.76 (s, 3H), 1.14 (t, 3H). LCMS (M + H$^+$) = 454.18. HPLC (Condition A): 2.86 min. |
| 68 | (1S)-1-phenylethyl | phenyl | 5-Methyl-4-[[2-methyl-5-[(phenylamino)carbonyl]phenyl]amino]-N-[(1S)-1-phenylethyl]pyrrolo[2,1-f][1,2,4]triazine-6-carboxamide | LCMS (M + H$^+$) = 505.27. HPLC (Condition A): 3.34 min. |
| 69 | (1S)-1-phenylethyl | 4-cyanophenyl | 4-[[5-[[(4-Cyano-phenyl)amino]carbonyl]-2-methylphenyl]amino]-5-methyl-N-[(1S)-1-phenylethyl]pyrrolo[2,1-f][1,2,4]triazine-6-carboxamide | LCMS (M + H$^+$) = 530.23. HPLC (Condition A): 3.35 min. |

EXAMPLE 70

N-Ethyl-4-[[5-[[(3-fluorophenyl)sulfonyl]amino]-2-methylphenyl]amino]-5-methylpyrrolo[2,1-f][1,2,4]triazine-6-carboxamide

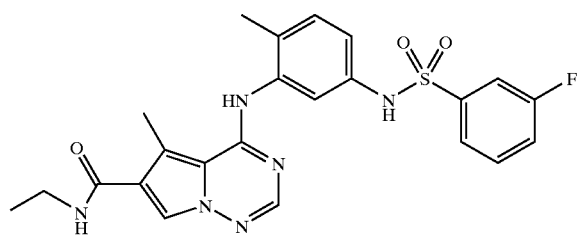

To a solution of 4-methyl-3-nitroaniline [compound (1a) from Scheme 8)(3.72 g, 24.5 mmol)] in 150 ml of DCM at rt was added 3-fluorobenzenesulfonyl chloride (5.00 g, 25.7 mmol), followed by TEA (7.0 ml, 50.2 mmol) via syringe. The resulting mixture was stirred for 20 h and the solvent removed in vacuo. The residue was dissolved in DCM (600 ml), washed with sat'd aq. NaHCO₃, dried over sodium sulfate, filtered, and concentrated in vacuo to give 8.00 g of dark solid which was triturated with DCM to afford 5.46 g of yellow solid. A portion of this solid (1.63 g) was dissolved in 10 ml 1N aq. NaOH and 20 ml THF, and the solution was stirred at rt for 20 h. The solvent was removed in vacuo and the residue acidified with 3N HCl to a pH of 2. The resulting precipitated solid was collected by filtration to afford 1.02 g (94%) of a light yellow solid as the desired Compound A. HPLC (Condition A)=2.99 min. $^1$HNMR(CDCl$_3$) δ 7.67 (d, 1H), 7.59 (dd, 1H), 7.49 (m, 2H), 7.32 (m, 1H), 7.28 (m, 2H), 2.54 (s, 3H).

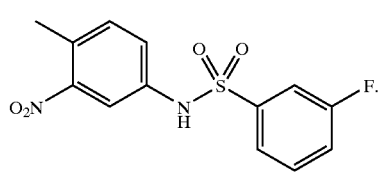

A

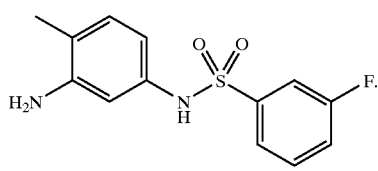

B

To 0.20 g (0.64 mmol) of Compound A in MeOH (10 ml) was added 10% Pd/C (20 mg) and the mixture stirred under hydrogen balloon for 6 h at rt. The solution was filtered through a pad of celite and the solvent removed in vacuo to give 0.18 g (100%) of Compound B as a colorless, glassy solid. HPLC (Conditions A): 1.77 min. LCMS M+H$^+$ (m/z) 281.

C.

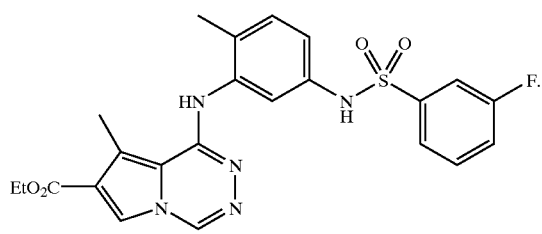

Compound B (0.18 g, 0.64 mmol) and 0.15 g (0.64 mmol) of 4-chloro-5-methylpyrrolotriazine-6-ethylcarboxylate (compound 8 of Scheme 8) in anhydrous DMF was stirred at rt for 20 h. The reaction was quenched with addition of cold water and sat'd aq. NaHCO₃. The solid was collected, washed with water, and dried in vacuo to give 0.27 g (91%) of Compound C as a light yellow solid. HPLC (Condition A: 3.49 min. LCMS M+H⁺ (m/z) 484.

D.

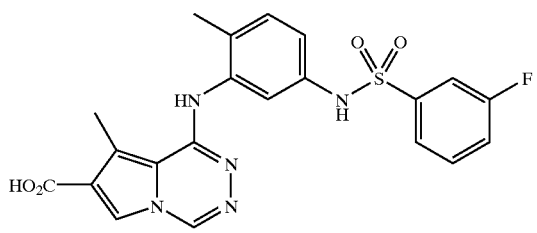

A solution of 0.27 g (56 mmol) of Compound C in 1 ml of 1N aq. NaOH and 3 ml of MeOH was heated at 60° C. for 12 hr. The MeOH was removed in vacuo and the aqueous portion acidified with 1N aq. hydrogen chloride to pH~2. The resulting precipitated solid was collected, washed with water, and dried in vacuo to afford 0.25 g (98%) of Compound D as a pale yellow solid. HPLC (Condition A): 2.93 min. LCMS M+H⁺ (m/z) 456.

E. A mixture of 30 mg (66 μmol) of Compound D, EDCI (19 mg, 98 μmol), HOBt (13 mg, 98 μmol) and Hunig's base (43 μL, 0.25 mmol) was stirred at rt for 0.5 hr. Ethylamine hydrochloride (10 mg, 0.13 mmol) was added and the mixture stirred for 16 hr. The crude mixture was purified by RP preparative HPLC chromatography to give Example 130. HPLC (Conditions A): 2.83 min. LCMS M+H⁺ (m/z) 483.

EXAMPLES 71–72

Examples 71 and 72 as shown in Table 5 were prepared from Compound D of Example 70 and an appropriate amine as described in Example 70, step E.

TABLE 5

| Ex | Compound | Compound Name | Data |
|----|----------|---------------|------|
| 71 | | 4-[[5-[[(3-Fluorophenyl)sulfonyl]amino]-2-methylphenyl]amino]-N-[(1S)-2-methoxy-1-methylethyl]-5-methylpyrrolo[2,1-f][1,2,4]triazine-6-carboxamide | HPLC (Condition A): 2.89 min. MH⁺ (m/z) 527. |
| 72 | | 4-[[5-[[(3-Fluorophenyl)sulfonyl]amino]-2-methylphenyl]amino]-5-methyl-N-[(1S)-1-phenylethyl]pyrrolo[2,1-f][1,2,4]triazine-6-carboxamide | HPLC (Condition A): 3.23 min. MH⁺ (m/z) 559. |

EXAMPLES 73–81

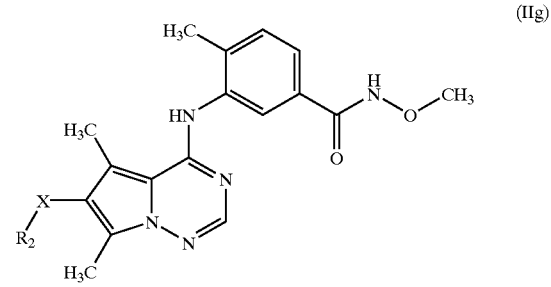

(IIg)

Compounds having the formula (IIg), wherein X and $R_2$ have the values listed in Table 6 were prepared from commercially-available diethyl-2,4-dimethylpyrrole-3,5-dicarboxylate following the same or similar procedure described above for the preparation of 5-desmethylpyrrolotriazine.

TABLE 6

| Ex | X | $R_2$ | Compound Name | Data |
|----|---|-------|---------------|------|
| 73 | —CO$_2$— | Et | 4-[[5-[(Methoxy-amino)carbonyl]-2-methylphenyl]amino]-5,7-dimethylpyrrolo[2,1-f][1,2,4]triazine-6-carboxylic acid ethyl ester | 398.2, M + H 3.13 min, A |
| 74 | —C(=O)NH— | Et | N-Ethyl-4-[[5-[(methoxy Amino)carbonyl]-2-methylphenyl]amino]-5,7-dimethylpyrrolo[2,1-f][1,2,4]triazine-6-carboxamide | 397.2, M + H 1.70 min, A |
| 75 | —C(=O)NH— | 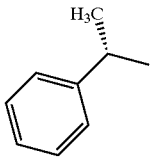 | 4-[[5-[(Methoxy-amino)carbonyl]-2-methylphenyl]amino]-5,7-dimethyl-N-[(1S)-1-phenylethyl]pyrrolo[2,1-f][1,2,4]triazine-6-carboxamide | 473.3, M + H 2.51 min, A |
| 76 | —C(=O)NH— | —CH(CH$_3$)$_2$ | 4-[[5-[(Methoxy-amino)carbonyl]-2-methylphenyl]amino]-5,7-dimethyl-N-(1-methylethyl)pyrrolo[2,1-f][1,2,4]triazine-6-carboxamide | 411.2, M + H 1.81 min, A |
| 77 | —C(=O)NH— | 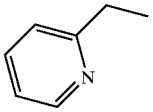 | 4-[[5-[(Methoxy-amino)carbonyl]-2-methylphenyl]amino]-5,7-dimethyl-N-(2-pyridinylmethyl)pyrrolo[2,1-f][1,2,4]triazine-6-carboxamide | 460.2, M + H 1.30 min, A |
| 78 | —CO$_2$— | H | 4-[[5-[(Methoxy amino)carbonyl]-2-methylphenyl]amino]-5,7-dimethylpyrrolo[2,1-f][1,2,4]triazine-6-carboxylic acid | 370.2, M + H 2.21 min, A |
| 79 | —C(=O)NH— | 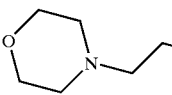 | 4-[[5-[(Methoxy-amino)carbonyl]-2-methylphenyl]amino]-5,7-dimethyl-N-[2-(4-morpholinyl)ethyl]pyrrolo[2,1-f][1,2,4]triazine-6-carboxamide | 482.1, M + H 1.21 min, A |
| 80 | —C(=O)NH— | 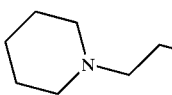 | 4-[[5-[(Methoxy-amino)carbonyl]-2-methylphenyl]amino]-5,7-dimethyl-N-[2-(1-piperidinyl)ethyl]pyrrolo[2,1-f][1,2,4]triazine-6-carboxamide | 480.2, M + H 1.39 min, A |
| 81 | —C(=O)NH— | 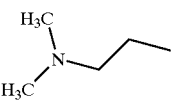 | N-[2-(Dimethylamino) Ethyl]-4-[[5-[(methoxy Amino)carbonyl]-2-methylphenyl]amino]-5,7-dimethylpyrrolo[2,1-f][1,2,4]triazine-6-carboxamide | 440.2, M + H 1.09 min, A |

EXAMPLE 82

4-[[5-[[(Ethylamino)carbonyl]amino]-2-methylphenyl]amino]-5-methyl-N-propyl pyrrolo[2,1-f][1,2,4]triazine-6-carboxamide

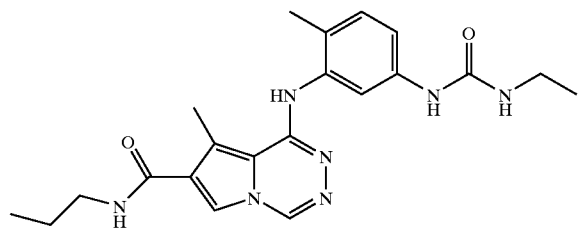

A. 5-Methyl-4-[(2-methyl-5-nitrophenyl)amino]pyrrolo[2,1-f][1,2,4]triazine-6-carboxylic acid ethyl ester

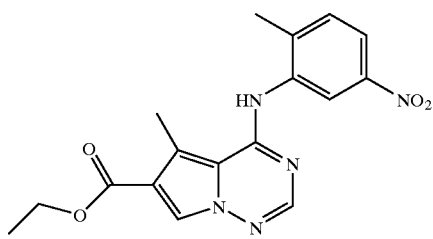

A suspension of chloropyrrolotriazine (2.03 g, 8.47 mmol) and 3-nitro-5-methyl aniline (1.41 g, 9.3 mmol) in DMF (25 mL) was stirred at rt for 24 h. Water (125 mL) was added over 30 min and the solution stirred for 1 h upon which the pH was adjusted to neutral with sat. aq. NaHCO$_3$. The solids were filtered, washed with water, and dried to give compound A (2.589 g, 85% yield) as a pale tan solid.

B. 5-Methyl-4-[(2-methyl-5-nitrophenyl)amino]pyrrolo[2,1-f][1,2,4]triazine-6-carboxylic Acid

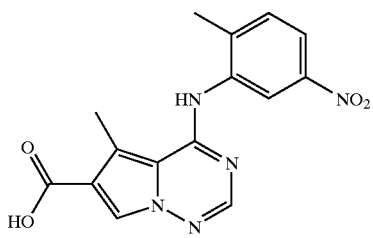

To a solution of Compound A (825 mg, 2.32 mmol) in THF (2 mL) and MeOH (1 mL) was added 1N NaOH (6 mL) and the reaction heated at 60° C. for 24 h. The reaction mixture was cooled, concentrated to remove the organic solvents, and the pH was adjusted to neutral with 1 N HCl. The solids were filtered, washed with water, and dried to give compound B. LCMS (M+H$^+$)=328.1. HPLC (Condition A): 3.40 min.

C. 5-methyl-4-[(2-methyl-5-nitrophenyl)amino]-N-propylpyrrolo[2,1-f][1,2,4]triazine-6-carboxamide

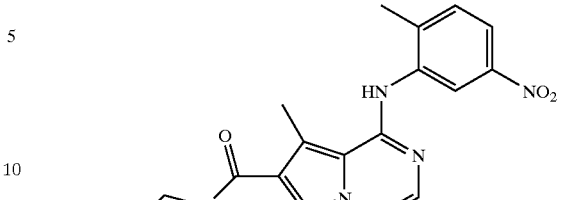

A solution of compound B (2.32 mmol), EDCI (489 mg, 2.55 mmol), and HOBt (345 mg, 2.55 mmol) in DMF (6 mL) was stirred at rt for 1 h, and then n-propyl amine (0.38 mL, 6.4 mmol) was added. The reaction was stirred for 4 h and water was added to precipitate the product. The solids were filtered and purified via column chromatography on silica (33% ethyl acetatehexanes) to give compound C (0.79 g, 93% yield) as a white solid. $^1$H NMR (CDCl$_3$): δ 9.11 (s, 1H), 7.92 (m, 2H), 7.71 (s, 1H), 7.36 (d, J=8.4 Hz, 1H), 5.82 (br m, 1H), 3.34 (q, J=6.7 Hz, 2H), 2.86 (s, 3H), 2.41 (s, 3H), 1.58 (m, 2H), 1.16 (t, J=7.5 Hz, 3H). LCMS (M+H$^+$)=369.3. HPLC (Condition A): 3.42 min.

D. 4-[(5-Amino-2-methylphenyl)amino]-5-methyl-N-propylpyrrolo[2,1-f][1,2,4]triazine-6-carboxamide

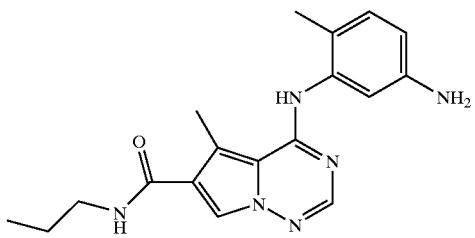

A solution of compound C (794 mg, 2.16 mmol) and 10% Pd/C (250 mg, wet) in MeOH (20 mL) was degassed and backfilled with hydrogen three times and stirred for 2 h. The solution was filtered and concentrated to give compound D (691 mg, 95% yield). $^1$H NMR (CDCl$_3$): δ 7.94 (s, 1H), 7.73 (s, 1H), 7.53 (s, 1H), 7.23 (m, 1H), 7.06 (d, J=8.1 Hz, 1H), 6.53 (dd, J=8.1, 2.2 Hz, 1H) 5.86 (br m, 1H), 3.43 (q, J=6.6 Hz, 2H), 2.91 (s, 3H), 2.27 (s, 3H), 1.68 (m, 2H), 1.02 (t, J=7.3 Hz, 3H). LCMS (M+H$^+$)=339.2. HPLC (Condition A): 2.39 min.

E. To a suspension of 25.6 g (0.076 mmol) of compound D in 0.3 mL of DCE was added 22 µL of ethyl isocyanate at rt. The reaction mixture was heated at 50° C. for 12 h, then cooled, and isopropanol was added (1 mL). The resulting precipitated product was collected by vacuum filtration and washed with 1 miil of isopropanol and dried in vacuo to afford 19.6 mg (63%) of the titled compound as a pure product. $^1$H NMR (CD$_3$OD): δ 7.94 (s, 1H), 7.70 (s, 1H), 7.60 (s, 1H), 7.23 (br s, 2H), 7.44 (d, 1H), 3.23 (q, 2H), 2.84 (s, 3H), 2.24 (s, 3H), 1.66 (m, 2H), 1.16 (t, 3H), 1.02 (t, 3H). LCMS (M+H$^+$)=410.2. HPLC (Condition A): 2.82 min.

EXAMPLES 83–88

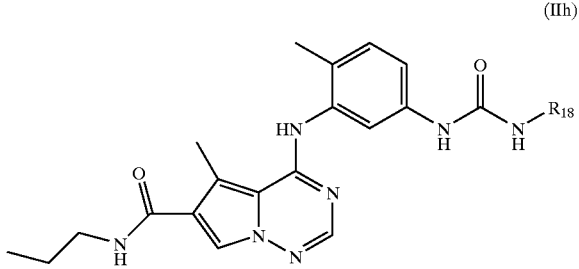

(IIh)

Compound having the formula (IIh), wherein $R_{18}$ has the values listed in Table 7 were prepared following the procedure outlined for Example 82, using different isocyanates in the last step.

TABLE 7

| Ex. | $R_{18}$ | Compound Name | Data MS/HPLC |
|---|---|---|---|
| 83 | | 5-Methyl-4-[[2-methyl-5-[[(phenylamino)carbonyl]-amino]phenyl]amino]-N-propylpyrrolo[2,1-f][1,2,4]triazine-6-carboxamide | 458.2 3.40 min |
| 84 | | 5-Methyl-4-[[2-methyl-5-[[[(3-methylphenyl)amino]-carbonyl]amino]phenyl]-amino]-N-propyl-pyrrolo[2,1-f][1,2,4]triazine-6-carboxamide | 472.5 3.60 |
| 85 | CN | 4-[[5-[[[(4-Cyanophenyl)-amino]carbonyl]amino]-2-methylphenyl]amino]-5-methyl-N-propyl-pyrrolo[2,1-f][1,2,4]triazine-6-carboxamide | 483.3 3.48 |
| 86 | Cl, Cl | 4-[[5-[[[(2,3-Dichloro-phenyl)amino]carbonyl]-amino]-2-methylphenyl]-amino]-5-methyl-N-propyl-pyrrolo[2,1-f][1,2,4]-triazine-6-carboxamide | 526.2 3.98 |
| 87 | F | 4-[[5-[[[(4-Fluorophenyl)-amino]carbonyl]amino]-2-methylphenyl]amino]-5-methyl-N-propyl-pyrrolo[2,1-f][1,2,4]triazine-6-carboxamide | 476.2 3.48 |
| 88 | CF3 | 5-Methyl-4-[[2-methyl-5-[[[[3-(trifluoromethyl)-phenyl]amino]carbonyl]-amino]phenyl]amino]-N-propylpyrrolo[2,1-f][1,2,4]triazine-6-carboxamide | 526.1 3.87 min |

EXAMPLES 89–92

The compounds named below were prepared using methods analogous to the procedures described hereinbefore:

89) 1,3-Dihydro-3-[5-methoxy-6-[[4-(4-methyl-1-piperazinyl)butyl]amino]pyrrolo[2,1-f][1,2,4]triazin-4-yl]-2H-indol-2-one;

90) 1,3-Dihydro-3-[5-methoxy-6-[[4-(4-morpholinyl)butyl]amino]pyrrolo[2,1-f][1,2,4]triazin-4-yl]-2H-indol-2-one;

91) 1-[3-[4-(2,3-Dihydro-2-oxo-1H-indol-3-yl)-5-methylpyrrolo[2,1-f][1,2,4]triazin-6-yl]-1-oxopropyl]-4-methylpiperazine; and 92) 2-Methyl-5-[[5-methyl-6-[3-(2H-1,2,3-triazol-2-yl)propoxy]pyrrolo[2,1-f][1,2,4]triazin-4-yl]amino]phenol.

We claim:

1. A method of forming an aminated pyrrole comprising: reacting a pyrrole compound of Formula IV:

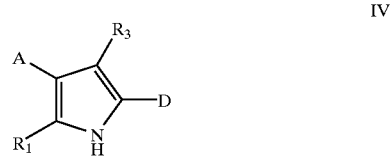

IV wherein $R_1$ is selected from H, alkyl, aralkyl, $OR_1'$, $OC(O)R_1'$, $OC(O)OR_1'$, $OC(O)NR_1'R_1''$, $OS(O)_2R_1'''$, and $OS(O)_2NR_1'R_1''$, wherein the groups $R_1'$ and $R_1''$ may each independently be H, alkyl, aryl, aralkyl, heterocyclo, or cycloalkyl groups, or may be taken together to form a cycloalkyl, aryl, or heterocyclic group, any of which may be optionally substituted, and the group $R_1'''$ is defined as an alkyl, aryl, aralkyl, heterocyclo, or cycloalkyl; —$SCH_3$, —$OC(=O)R_{21}$, —$S(=O)R_{22}$, —$SO_2R_{22}$, —$SO_2NR_{24}R_{25}$, —$CO_2R_{21}$, —$C(=O)NR_{24}R_{25}$, —$NH_2$, —$NR_{24}R_{25}$, —$NR_{21}SO_2NR_{24}R_{25}$, —$NR_{21}SO_2R_{22}$, —$NR_{24}C(=O)R_{25}$, —$NR_{24}CO_2R_{25}$, —$NR_{21}C(=O)NR_{24}R_{25}$, halogen, nitro, or cyano;

A is selected from $R_2X$ or E, where X is selected from —O—, —$OC(=O)$—, —S—, —$S(=O)$—, —$SO_2$—, —$C(=O)$—, —$CO_2$—, —$NR_{10}$—, —$NR_{10}C(=O)$—, —$NR_{10}C(=O)NR_{11}$—, —$NR_{10}CO_2$—, —$NR_{10}SO_2$—, —$NR_{10}SO_2NR_{11}$—, —$SO_2NR_{10}$—, —$C(=O)NR_{10}$—, halogen, nitro, and cyano, or X is absent; and E is an electron withdrawing group; or $R_1$, taken together with A, can form an optionally substituted saturated or unsaturated aromatic or heterocyclic ring;

$R_2$ is selected from:
(i) hydrogen, provided that $R_2$ is not hydrogen if X is —$S(=O)$—, —$SO_2$—, —$NR_{10}CO_2$—, or —$NR_{10}SO_2$—;
(ii) alkyl, alkenyl, and alkynyl optionally substituted with up to four $R_{26}$;
(iii) aryl and heteroaryl optionally substituted with up to three $R_{27}$;
(iv) heterocyclo and cycloalkyl optionally substituted with keto (=O), up to three $R_{27}$, and/or having a carbon-carbon bridge of 3 to 4 carbon atoms; or
(v) —$C(O)R^b$ where $R^b$ is H, OH, alkyl, aralkyl, halo, $OR^{b'}$, $OC(O)R^{b'}$, $OC(O)OR^{b'}$, $OC(O)NR^bR^{b'}$, $OS(O)R^{b'}$, $OS(O)NR^bR^{b'}$, and $R^b$ and $R^{b'}$ are each independently selected from H, alkyl, aralkyl, heterocyclo or cycloalkyl, or $R^b$ and $R^{b'}$ together form a cycloalkyl, aryl or heterocyclo group; however $R_2$ is absent if X is halogen, nitro or cyano;

$R_3$ is selected from H, OH, $C_1$–$C_6$ alkoxy, alkyl, $C_1$–$C_6$ perfluoroalkyl, —O—($C_1$–$C_6$) perfluoroalkyl, cycloalkyl, heterocyclo, aryl, aralkyl, acyl, carbalkoxy, carboxamido, cyano, halogen, amine, substituted amine, $NO_2$, $OR_3'$, $CH_2OR_3'$, $CH_2NR_3'R_3''$, $CH_2SR_3'$, $OC(O)R_3'$, $OC(O)OR_3''$, $OC(O)NR_3'R_3''$, $OS(O)_2R_3'$, and $OS(O)_2NR_3'R_3''$; the $R_3'$ and $R_3''$ groups are each independently H, alkyl, aralkyl, heterocycle, cycloalkyl, or aryl. $R_3'$ and $R_3''$ when taken together may form a cycloalkyl, aryl, or heterocyclic group, any of which may be optionally substituted;

$R_{21}$, $R_{24}$, and $R_{25}$ are independently selected from hydrogen, alkyl, substituted alkyl, aryl, substituted aryl, heterocyclo, and substituted heterocyclo;

$R_{10}$ and $R_{11}$ are independently selected from hydrogen, alkyl, substituted alkyl, aryl, substituted aryl, cycloalkyl, substituted cycloalkyl, heterocyclo, and substituted heterocyclo;

$R_{22}$ is selected from alkyl, substituted alkyl, aryl, substituted aryl, heterocyclo, or substituted heterocyclo;

$R_{26}$ is selected from halogen, trifluoromethyl, haloalkoxy, oxo (=O), nitro, cyano, $-SR_{28}$, $-OR_{28}$, $-NR_{28}R_{29}$, $-NR_{28}SO_2$, $-NR_{28}SO_2R_{29}$, $-SO_2R_{28}$, $-SO_2NR_{28}R_{29}$, $-CO_2R_{28}$, $-C(=O)R_{28}$, $-C(=O)NR_{28}R_{29}$, $-OC(=O)R_{28}$, $-OC(=O)NR_{28}R_{29}$, $-NR_{28}C(=O)R_{29}$, $-NR_{28}CO_2R_{29}$, =N—OH, =N—O-alkyl; aryl optionally substituted with one to three $R_{27}$; cycloalkyl optionally substituted with oxo (=O), one to three $R_{27}$, or having a carbon-carbon bridge of 3 to 4 carbon atoms; and heterocyclo optionally substituted with oxo (=O), one to three $R_{27}$, or having a carbon-carbon bridge of 3 to 4 carbon atoms; wherein $R_{28}$ and $R_{29}$ are each independently selected from hydrogen, alkyl, alkenyl, aryl, aralkyl, $C_{3-7}$cycloalkyl, and $C_{3-7}$heterocycle, or may be taken together to form a $C_{3-7}$heterocycle; and wherein each $R_{28}$ and $R_{29}$ in turn is optionally substituted with up to two of alkyl, alkenyl, halogen, haloalkyl, haloalkoxy, cyano, nitro, amino, hydroxy, alkoxy, alkylthio, phenyl, benzyl, phenyloxy, and benzyloxy;

$R_{27}$ is selected from alkyl, $R_{32}$, and $C_{1-4}$alkyl substituted with one to three $R_{32}$, wherein each $R_{32}$ group is independently selected from halogen, haloalkyl, haloalkoxy, nitro, cyano, $-SR_{30}$, $-OR_{30}$, $-NR_{30}R_{31}$, $-NR_{30}SO_2$, $-NR_{30}SO_2R_{31}$, $-SO_2R_{30}$, $-SO_2NR_{30}R_{31}$, $-CO_2R_{30}$, $-C(=O)R_{30}$, $-C(=O)NR_{30}R_{31}$, $-OC(=O)R_{30}$, $-OC(=O)NR_{30}R_{31}$, $-NR_{30}C(=O)R_{31}$, $-NR_{30}CO_2R_{31}$, and a 3 to 7 membered carbocyclic or heterocyclic ring optionally substituted with alkyl, halogen, hydroxy, alkoxy, haloalkyl, haloalkoxy, nitro, amino, or cyano, wherein $R_{30}$ and $R_{31}$ are each independently selected from hydrogen, alkyl, alkenyl, aryl, aralkyl, $C_{3-7}$cycloalkyl, and heterocycle, or may be taken together to form a $C_{3-7}$ heterocycle; and D is selected from the group consisting of —CHO, CN, $-COR_p$, $-C(=O)OR_p$, and $R_qC(O)NH-$, where $R_p$ and $R_q$ are each independently selected from H or substituted or unsubstituted $C_1-C_6$ alkyl, aryl or halogenated alkyl; with chloramine in the presence of a base to form a compound of Formula V:

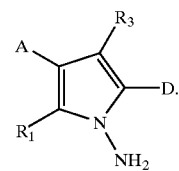

2. A method of preparing a compound of formula VI,

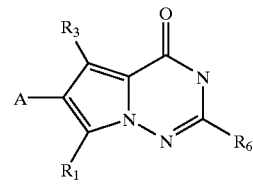

wherein:

$R_1$ is selected from H, alkyl, aralkyl, $OR_1'$, $OC(O)R_1'$, $OC(O)OR_1'$, $OC(O)NR_1'R_1''$, $OS(O)_2R_1'''$, and $OS(O)_2NR_1'R_1''$, wherein the groups $R_1'$ and $R_1''$ may each independently be H, alkyl, aryl, aralkyl, heterocyclo, or cycloalkyl groups, or may be taken together to form a cycloalkyl, aryl, or heterocyclic group, any of which may be optionally substituted, and the group $R_1'''$ is defined as an alkyl, aryl, aralkyl, heterocyclo, or cycloalkyl; $-SCH_3$, $-OC(=O)R_{21}$, $-S(=O)R_{22}$, $-SO_2R_{22}$, $-SO_2NR_{24}R_{25}$, $CO_2R_{21}$, $-C(=O)NR_{24}R_{25}$, $-NH_2$, $-NR_{24}R_{25}$, $-NR_{21}SO_2NR_{24}R_{25}$, $-NR_{21}SO_2R_{22}$, $-NR_{24}C(=O)R_{25}$, $-NR_{24}CO_2R_{25}$, $-NR_{21}C(=O)NR_{24}R_{25}$, halogen, nitro, or cyano;

A is $R_2X$ or E, where X is selected from —O—, —OC(=O)—, —S—, —S(=O)—, $-SO_2-$, $-C(=O)-$, $-CO_2-$, $-NR_{10}-$, $-NR_{10}C(=O)-$, $-NR_{10}C(=O)NR_{11}-$, $-NR_{10}CO_2-$, $-NR_{10}SO_2-$, $-NR_{10}SO_2NR_{11}-$, $-SO_2NR_{10}-$, $-C(=O)NR_{10}-$, halogen, nitro, and cyano, or X is absent; and E is an electron withdrawing group; or $R_1$, taken together with A, can form an optionally substituted saturated or unsaturated aromatic or heterocyclic ring;

$R_2$ is selected from:
  (i) hydrogen, provided that $R_2$ is not hydrogen if X is $-S(=O)-$, $-SO_2-$, $-NR_{10}CO_2-$, or $-NR_{10}SO_2-$;
  (ii) alkyl, alkenyl, and alkynyl optionally substituted with up to four $R_{26}$;
  (iii) aryl and heteroaryl optionally substituted with up to three $R_{27}$;
  (iv) heterocyclo and cycloalkyl optionally substituted with oxo (=O), up to three $R_{27}$, and/or having a carbon-carbon bridge of 3 to 4 carbon atoms; and
  (v) $-C(O)R^b$ where $R^b$ is H, OH, alkyl, aralkyl, halo, $OR^{b'}$, $OC(O)R^{b'}$, $OC(O)OR^{b'}$, $OC(O)NR^bR^{b'}$, $OS(O)R^{b'}$, $OS(O)NR^bR^{b'}$, and $R^b$ and $R^{b'}$ are each independently selected from H, alkyl, aralkyl, heterocyclo or cycloalkyl, or $R^b$ and $R^{b'}$ together form a cycloalkyl, aryl or heterocyclo group; however $R_2$ is absent if X is halogen, nitro or cyano;

$R_3$ is selected from H, OH, $C_1$–$C_6$ alkoxy, alkyl, $C_1$–$C_6$ perfluoroalkyl, —O—$C_1$–$C_6$ perfluoroalkyl, cycloalkyl, heterocyclo, aryl, aralkyl, acyl, carbalkoxy, carboxamido, cyano, halogen, amine, substituted amine, $NO_2$, $OR_3'$, $CH_2OR_3'$, $CH_2NR_3'R_3''$, $CH_2SR_3'$, $OC(O)R_3'$, $OC(O)OR_3'$, $OC(O)NR_3'R_3''$, $OS(O)_2R_3'$, and $OS(O)_2NR_3'R_3''$; the $R_3'$ and $R_3''$ groups are each independently H, alkyl, aralkyl, heterocycle, cycloalkyl, or aryl. $R_3'$ and $R_3''$ when taken together may form a cycloalkyl, aryl, or heterocyclic group, any of which may be optionally substituted;

$R_6$ is;

$R_7$ and $R_8$ are each independently selected from hydrogen, alkyl, substitute alkyl, aryl, substituted aryl, heterocylco, and substituted heterocyclo;

$R_{10}$ and $R_{11}$ are independently selected from hydrogen, alkyl, substituted alkyl, aryl, substituted aryl, cycloalkyl, substituted cycloalkyl, heterocyclo, and substituted heterocyclo;

$R_{21}$, $R_{24}$, and $R_{25}$ are independently selected from hydrogen, alkyl, substituted alkyl, aryl, substituted aryl, heterocyclo, and substituted heterocyclo;

$R_{22}$ is alkyl, substituted alkyl, aryl, substituted aryl, heterocyclo, or substituted heterocyclo;

comprising:

(a) reacting a compound of formula IV,

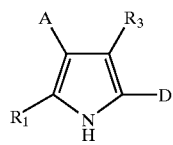

IV wherein $R_1$, A and $R_3$ are defined as hereinabove, and

D is —C(=O)$OR_p$ wherein $R_p$ is selected from H or substituted or unsubstituted $C_1$–$C_6$ alkyl or aryl;

with chloramine in the presence of a base to form a compound of Formula V,

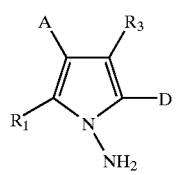

V wherein $R_1$, A, $R_3$ and D are defined as hereinabove;

(b) further reacting the compound of formula V with an amide of formula $R_6C(=O)NH_2$, wherein $R_6$ is defined as hereinabove, to form the compound of formula VI.

3. The method of claim 2, further comprising:

(a) reacting the compound of formula VI with a halogenating agent to form a compound of formula VII:

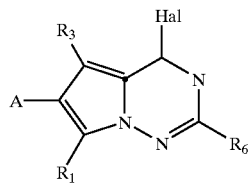

VII wherein Hal is a selected from F, Cl and Br;

(b) further reacting the compound formula VII with a reactant B—$ZR_4R_5$; wherein:

Z is selected from O, S or N;

B is H;

$R_4$ is substituted aryl, aryl substituted with $NHSO_2$alkyl, substituted heteroaryl, or an optionally-substituted bicyclic 7–11 membered saturated or unsaturated carbocyclic or heterocyclic ring; and $R_5$ is hydrogen, alkyl, or substituted alkyl; provided that when Z is O or S, one of $R_4$ or $R_5$ is absent; or alternatively, $R_4$ and $R_5$ taken together with Z form an optionally substituted aryl, or an optionally-substituted bicyclic 7–11 membered aryl or heteroaryl; wherein in either case the substitution of the aryl or the bicyclic aryl or heteroaryl may be by a substituted or unsubstituted alkyl, cycloalkyl, aryl or heteroaryl substituent;

to form a compound of Formula I,

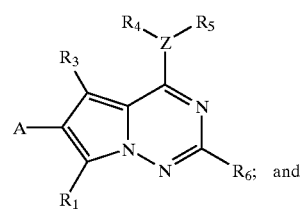

(I)

(c) optionally, further reacting the compound of Formula (I) to form a pharmaceutically acceptable salt or solvate thereof.

4. The method of claim 3 wherein, in the reactant B—$ZR_4R_5$ of step (b), $R_4$ is substituted aryl with one or more substituents Y—$R_{18}$, where Y is C or N and $R_{18}$ is selected from hydrogen, alkyl, substituted alkyl, cycloalkyl, aryl, substituted aryl, heterocyclo and substituted heterocyclo; and $R_5$ is H or substituted alkyl.

5. The method of claim 3 wherein the reactant B—$ZNR_4R_5$ used in step (b) is a compound of the formula VIII:

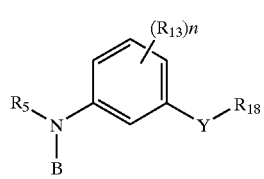

VIII wherein Y is selected from —C(=O)$NR_{23}$—, —$NR_{23}$C(=O)$NR_{23}$—, —$NR_{23}SO_2$—, or —$SO_2NR_{23}$—;

B is H;

$R_5$ is hydrogen or alkyl; $R_{13}$ is selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, and aryloxy, and each $R_{13}$ may be further substituted by hydroxy, alkyl, alkoxy, aryl, or aralkyl, and n is an integer between 1 and 3;

$R_{18}$ and $R_{23}$ are each independently selected from hydrogen, alkyl, cycloalkyl, heterocyclo, alkoxy, aryl, and aryl/heterocyclo substituted with one to three $R_{19}$, except that when Y is —$NR_{23}SO_2$—, $R_{18}$ is $C_{1-4}$alkyl or aryl optionally substituted with one to three $R_{19}$; and $R_{13}$ and $R_{19}$ at each occurrence is independently selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, and aryloxy, wherein each $R_{13}$ and/or $R_{19}$ group may be further substituted by hydroxy, alkyl, alkoxy, aryl, or aralkyl.

6. The method of claim 5 wherein the reactant B—$ZNR_4R_5$ used in step (b) is:

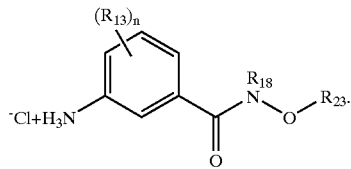

7. The method of claim 3 further comprising reacting the compound of formula I, wherein $R_2$ is H and X is —COO—, with an amine of formula $R_{10}R_2NH$, using an amide coupling agent, to form a compound of formula IIB:

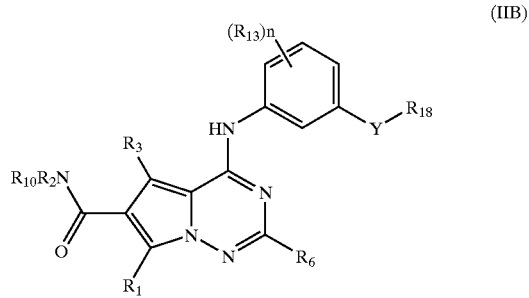

(IIB)

wherein
$R_{13}$ is selected from alkyl, halo, trifluoromethoxy, trifluoromethyl, hydroxy, alkoxy, alkanoyl, alkanoyloxy, thiol alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, and aryloxy, wherein each $R_{13}$ and/or $R_{19}$ group may be further substituted by hydroxy, alkyl, alkoxy, aryl, or aralkyl; and $R_{18}$ is selected from hydrogen, alkyl, substituted alkyl, cycloalkyl, aryl, substituted aryl, heterocyclo and substituted heterocyclo.

8. The method of claim 2 wherein in step (a), in the pyrrole of formula IV:

$R_1$ is selected from hydrogen, —$CH_3$, —OH, —$OCH_3$, —SH, —$SCH_3$, —$OC(=O)R_{21}$, —$S(=O)R_{22}$, —$SO_2R_{22}$, —$SO_2NR_{24}R_{25}$, —$CO_2R_{21}$, —$C(=O)NR_{24}R_{25}$, —$NH_2$, —$NR_{21}SO_2NR_{24}R_{25}$, —$NR_{21}SO_2R_{22}$, —$NR_{24}C(=O)R_{25}$, —$NR_{24}CO_2R_{25}$, —$NR_{21}C(=O)NR_{24}R_{25}$, halogen, nitro or cyano;

$R_3$ is selected from H, OH, $C_1$–$C_6$ alkoxy, alkyl, $C_1$–$C_6$ perfluoroalkyl, —O—$C_1$–$C_6$ perfluoroalkyl, cycloalkyl, heterocyclo, aryl, aralkyl, acyl, carbalkoxy, carboxamido, cyano, halogen, amine, substituted amine, $NO_2$, $OR_3'$, $CH_2OR_3'$, $CH_2NR_3'R_3''$, $CH_2SR_3'$, $OC(O)R_3'$, $OC(O)OR_3''$, $OC(O)NR_3'R_3''$, $OS(O)_2R_3'$, and $OS(O)_2NR_3'R_3''$; the $R_3'$ and $R_3''$ groups are each independently H, alkyl, aralkyl, heterocycle, cycloalkyl, or aryl. $R_3'$ and $R_3''$ when taken together may form a cycloalkyl, aryl, or heterocyclic group, any of which may be optionally substituted;

A is $R_2X$; and X is selected from —$C(=O)$—, —$CO_2$—, —$NR_{10}C(=O)$—, and —$C(=O)NR_{10}$—, or X is absent;

$R_2$ is selected from hydrogen, $C_{2-6}$alkyl, substituted $C_{1-4}$alkyl, aryl, aralkyl, substituted aryl, substituted aralkyl, cycloalkyl, substituted cycloalkyl, heterocycle, or substituted heterocycle, or optionally-substituted cycloalkylalkyl or heterocycloalkyl;

$R_4$ is selected from aryl or heteroaryl substituted with one $R_{12}$ and zero to three $R_{13}$;

$R_5$ and $R_{10}$ independently are selected from hydrogen and lower alkyl;

$R_6$ is selected from hydrogen, alkyl, substituted alkyl, aryl, substituted aryl, heterocyclo, substituted heterocyclo, —$NR_7R_8$, —$OR_7$, or halogen;

$R_{12}$ is selected from carbamyl, sulfonamido, arylsulfonylamine, or ureido, each of which is optionally substituted with up to two of hydroxy, alkyl, substituted alkyl, alkoxy, aryl, substituted aryl, and aralkyl, or $R_{12}$ is alkylsulfonylamine;

$R_{13}$ at each occurrence is independently selected from alkyl, substituted alkyl, halo, trifluoromethoxy, trifluoromethyl, —$OR_{14}$, —$C(=O)$alkyl, —$OC(=O)$alkyl, —$NR_{15}R_{16}$, —$SR_{15}$, —$NO_2$, —CN, —$CO_2R_{15}$, —$CONH_2$, —$SO_3H$, —$S(=O)$alkyl, —$S(=O)$aryl, —$NHSO_2$-aryl-$R_{17}$, —$NHSO_2$-alkyl, —$SO_2NHR_{17}$, —$CONHR_{17}$, and —$NHC(=O)NHR_{17}$;

$R_{14}$ is selected from hydrogen, alkyl, or aryl;

$R_{15}$ is selected from hydrogen or alkyl;

$R_{16}$ is selected from hydrogen, alkyl, aralkyl, or alkanoyl;

$R_{17}$ is selected from hydrogen, hydroxy, alkyl, substituted alkyl, alkoxy, aryl, substituted aryl, or aralkyl; and $R_7$, $R_8$, $R_{10}$, $R_{11}$, $R_{21}$, $R_{24}$, and $R_{25}$ are independently selected from hydrogen and alkyl; and $R_{22}$ is alkyl or substituted alkyl.

9. The method of claim 2 wherein step (b) is performed in the presence of an acid.

* * * * *

UNITED STATES PATENT AND TRADEMARK OFFICE
CERTIFICATE OF CORRECTION

PATENT NO. : 6,867,300 B2
DATED : March 15, 2005
INVENTOR(S) : Godfrey, Jr. et al.

It is certified that error appears in the above-identified patent and that said Letters Patent is hereby corrected as shown below:

Column 59,
Line 13, should read -- $R_6$ is hyrdrogen --

Signed and Sealed this

Nineteenth Day of July, 2005

JON W. DUDAS
*Director of the United States Patent and Trademark Office*

UNITED STATES PATENT AND TRADEMARK OFFICE
CERTIFICATE OF CORRECTION

PATENT NO.       : 6,867,300 B2  
APPLICATION NO.  : 10/289010  
DATED            : March 15, 2005  
INVENTOR(S)      : Jollie Duane Godfrey, Jr. et al.

Page 1 of 1

It is certified that error appears in the above-identified patent and that said Letters Patent is hereby corrected as shown below:

In the claims:
Column 60, "Structure VII"

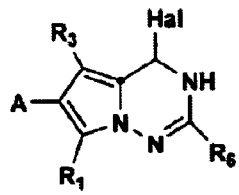

Should be replaced with the following structure.

Signed and Sealed this

Seventeenth Day of October, 2006

JON W. DUDAS  
*Director of the United States Patent and Trademark Office*